United States Patent
Bono et al.

(10) Patent No.: US 11,000,306 B2
(45) Date of Patent: May 11, 2021

(54) ROTARY OSCILLATING/RECIPROCATING SURGICAL TOOL

(71) Applicant: Peter L. Bono, Bingham Farms, MI (US)

(72) Inventors: Peter L. Bono, Bingham Farms, MI (US); James D. Lark, West Bloomfield, MI (US); John S. Scales, Ann Arbor, MI (US)

(73) Assignee: Peter L. Bono, Bingham Farms, MI (US)

( * ) Notice: Subject to any disclaimer, the term of this patent is extended or adjusted under 35 U.S.C. 154(b) by 136 days.

(21) Appl. No.: 16/168,011

(22) Filed: Oct. 23, 2018

(65) Prior Publication Data

US 2019/0117249 A1   Apr. 25, 2019

Related U.S. Application Data

(60) Provisional application No. 62/575,775, filed on Oct. 23, 2017.

(51) Int. Cl.
| | | |
|---|---|---|
| *A61B 17/32* | (2006.01) | |
| *A61B 17/16* | (2006.01) | |
| *A61B 17/00* | (2006.01) | |

(52) U.S. Cl.
CPC .... *A61B 17/32002* (2013.01); *A61B 17/1624* (2013.01); *A61B 17/1628* (2013.01); *A61B 17/1631* (2013.01); *A61B 17/1671* (2013.01); *A61B 17/1626* (2013.01); *A61B 2017/00398* (2013.01); *A61B 2017/00477* (2013.01); *A61B 2017/00734* (2013.01); *A61B 2017/320028* (2013.01)

(58) Field of Classification Search
CPC .. A61B 17/32002; A61B 2017/320028; A61B 2017/320032
See application file for complete search history.

(56) References Cited

U.S. PATENT DOCUMENTS

| | | | |
|---|---|---|---|
| 1,154,159 | A | 9/1915 | Ashworth |
| 2,557,429 | A | 6/1951 | Hawley |
| 2,831,295 | A | 4/1958 | Weiss |
| 3,091,060 | A | 5/1963 | Giegerich et al. |
| 3,554,197 | A | 1/1971 | Dobbie |
| 4,007,528 | A | 2/1977 | Shea et al. |
| 4,008,720 | A | 2/1977 | Brinckmann et al. |
| 4,081,704 | A | 3/1978 | Vassos et al. |
| RE29,736 | E | 8/1978 | Shea et al. |
| D248,967 | S | 8/1978 | Shea et al. |
| 4,111,208 | A | 9/1978 | Leuenberger |
| 4,596,243 | A | 6/1986 | Bray |
| 4,620,539 | A | 11/1986 | Andrews et al. |
| 4,828,052 | A | 5/1989 | Duran et al. |

(Continued)

FOREIGN PATENT DOCUMENTS

| | | |
|---|---|---|
| AR | 42807 | 7/2005 |
| AT | 370608 | 4/1983 |

(Continued)

*Primary Examiner* — Alexander J Orkin
(74) *Attorney, Agent, or Firm* — McHale & Slavin, P.A.

(57) ABSTRACT

A surgical tool that has a pair of transmissions coupled to one another to effect driving of a cutting tool in both an oscillating manner and a reciprocating manner. The transmissions are driven by a motor coupled to one of the transmissions.

17 Claims, 19 Drawing Sheets

(56) References Cited

U.S. PATENT DOCUMENTS

| | | | |
|---|---|---|---|
| 4,932,935 A | 6/1990 | Swartz | |
| 5,092,875 A | 3/1992 | McLees | |
| 5,522,829 A | 6/1996 | Michalos | |
| 5,733,119 A | 3/1998 | Carr | |
| 5,843,110 A | 12/1998 | Dross et al. | |
| 5,925,055 A * | 7/1999 | Adrian | A61B 17/22012 604/22 |
| 6,021,538 A | 2/2000 | Kressner et al. | |
| 6,032,673 A * | 3/2000 | Savage | A61B 18/1485 128/898 |
| 6,110,174 A | 8/2000 | Lichter | |
| 6,635,067 B2 | 10/2003 | Norman | |
| 6,689,087 B2 | 2/2004 | Pal et al. | |
| 6,716,215 B1 | 4/2004 | David et al. | |
| 6,721,986 B2 | 4/2004 | Zhuan | |
| 6,843,793 B2 | 1/2005 | Brock et al. | |
| 6,966,912 B2 | 11/2005 | Michelson | |
| 7,090,683 B2 | 8/2006 | Brock et al. | |
| 7,160,304 B2 | 1/2007 | Michelson | |
| 7,922,720 B2 | 4/2011 | May et al. | |
| 8,029,523 B2 | 10/2011 | Wallis et al. | |
| 8,038,630 B2 | 10/2011 | Pal et al. | |
| 8,465,491 B2 | 6/2013 | Yedlicka et al. | |
| 8,657,821 B2 | 2/2014 | Palermo | |
| 8,728,085 B2 | 5/2014 | Marsh et al. | |
| 8,828,001 B2 | 9/2014 | Stearns et al. | |
| 2004/0054355 A1 | 3/2004 | Gerbi et al. | |
| 2004/0147934 A1 | 7/2004 | Kiester | |
| 2005/0283175 A1 | 12/2005 | Tanner et al. | |
| 2006/0074442 A1 * | 4/2006 | Noriega | A61M 25/09 606/159 |
| 2006/0229624 A1 | 10/2006 | May et al. | |
| 2006/0235305 A1 | 10/2006 | Cotter et al. | |
| 2006/0235306 A1 | 10/2006 | Cotter et al. | |
| 2007/0156157 A1 | 7/2007 | Nahum et al. | |
| 2007/0282344 A1 | 12/2007 | Yedlicka et al. | |
| 2007/0282345 A1 | 12/2007 | Yedlicka et al. | |
| 2008/0027449 A1 | 1/2008 | Gundlapalli et al. | |
| 2008/0061784 A1 | 3/2008 | Pal et al. | |
| 2008/0064927 A1 | 3/2008 | Larkin et al. | |
| 2008/0108010 A1 | 5/2008 | Wang | |
| 2008/0154389 A1 | 6/2008 | Smith et al. | |
| 2008/0213899 A1 | 9/2008 | Olgac | |
| 2008/0269602 A1 | 10/2008 | Csavoy et al. | |
| 2009/0326537 A1 | 12/2009 | Anderson | |
| 2010/0145343 A1 | 6/2010 | Johnson et al. | |
| 2010/0165793 A1 | 7/2010 | Haug | |
| 2010/0249786 A1 | 9/2010 | Schmieding et al. | |
| 2011/0015635 A1 | 1/2011 | Aryan | |
| 2011/0196404 A1 | 8/2011 | Dietz et al. | |
| 2011/0230886 A1 | 9/2011 | Gustilo et al. | |
| 2011/0245833 A1 | 10/2011 | Anderson | |
| 2011/0295270 A1 | 12/2011 | Giordano et al. | |
| 2012/0186372 A1 | 7/2012 | Smith et al. | |
| 2012/0211546 A1 | 8/2012 | Shelton, IV | |
| 2013/0178856 A1 | 7/2013 | Ye et al. | |
| 2013/0206441 A1 | 8/2013 | Roser et al. | |
| 2013/0245629 A1 | 9/2013 | Xie | |
| 2013/0304069 A1 | 11/2013 | Bono et al. | |
| 2014/0088600 A1 * | 3/2014 | Carusillo | A61B 17/14 606/82 |
| 2014/0100574 A1 | 4/2014 | Bono et al. | |
| 2014/0222003 A1 | 8/2014 | Herndon et al. | |
| 2014/0262408 A1 | 9/2014 | Woodward | |
| 2014/0275955 A1 | 9/2014 | Crawford et al. | |
| 2014/0350571 A1 | 11/2014 | Maillet et al. | |
| 2015/0119916 A1 | 4/2015 | Dietz et al. | |
| 2015/0133960 A1 | 5/2015 | Lohmeier et al. | |
| 2015/0258333 A1 * | 9/2015 | Carver | A61B 17/32 606/129 |

FOREIGN PATENT DOCUMENTS

| | | |
|---|---|---|
| AU | 2003200831 | 11/2006 |
| AU | 2011215901 | 8/2012 |
| BE | 861446 | 3/1978 |
| CA | 1112970 | 11/1981 |
| CA | 2513071 | 7/2004 |
| CA | 2788918 | 8/2011 |
| CH | 610753 | 5/1979 |
| CL | 252004 | 3/2005 |
| CN | 102781349 | 11/2012 |
| DE | 2730227 | 6/1978 |
| DK | 570977 | 6/1979 |
| EP | 0148304 | 7/1985 |
| EP | 0261260 | 3/1988 |
| EP | 1571581 | 9/2005 |
| EP | 1581374 | 8/2006 |
| EP | 1690649 | 8/2006 |
| EP | 2533703 | 12/2012 |
| ES | 465719 | 12/1980 |
| FI | 773650 | 6/1978 |
| FR | 2374886 | 7/1978 |
| GB | 1550577 | 8/1979 |
| IT | 1081824 | 5/1985 |
| JP | S5613462 | 7/1978 |
| JP | 2006512954 | 4/2006 |
| JP | 2013519434 A | 5/2013 |
| JP | S5380789 | 1/2014 |
| JP | 4481173 | 6/2015 |
| JP | 5826771 | 12/2015 |
| NL | 7713563 | 6/1978 |
| NO | 774411 | 6/1978 |
| WO | WO08504903 | 11/1985 |
| WO | WO9107116 | 5/1991 |
| WO | WO0215799 | 2/2002 |
| WO | WO2004062863 | 7/2004 |
| WO | WO2007008703 | 1/2007 |
| WO | WO2009151926 | 12/2009 |
| WO | WO2011100313 | 8/2011 |
| WO | WO2012166476 | 12/2012 |
| WO | WO2014150514 | 9/2014 |
| WO | WO2015006296 | 1/2015 |
| WO | WO2015166487 | 11/2015 |
| WO | WO2015168069 | 11/2015 |

\* cited by examiner

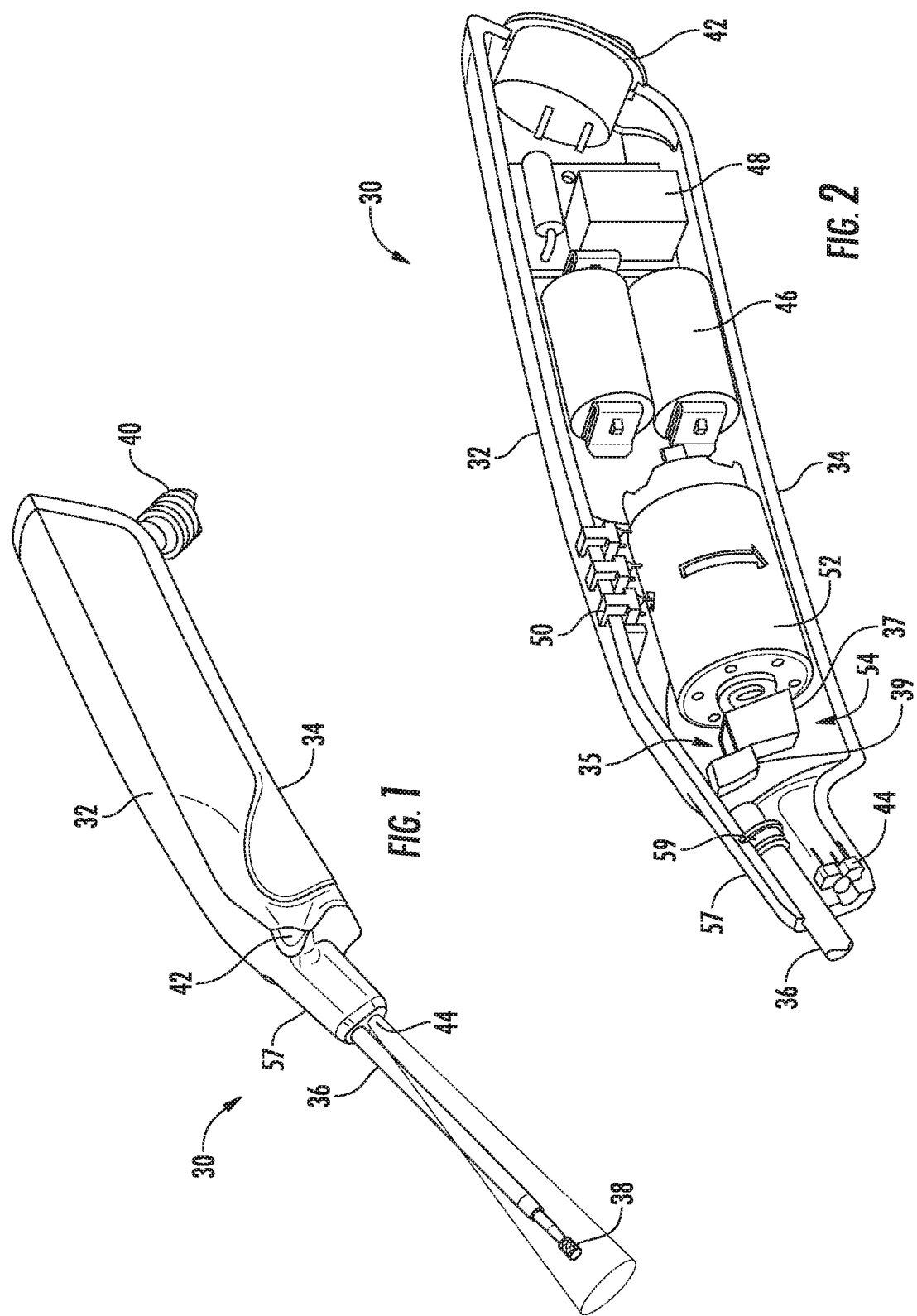

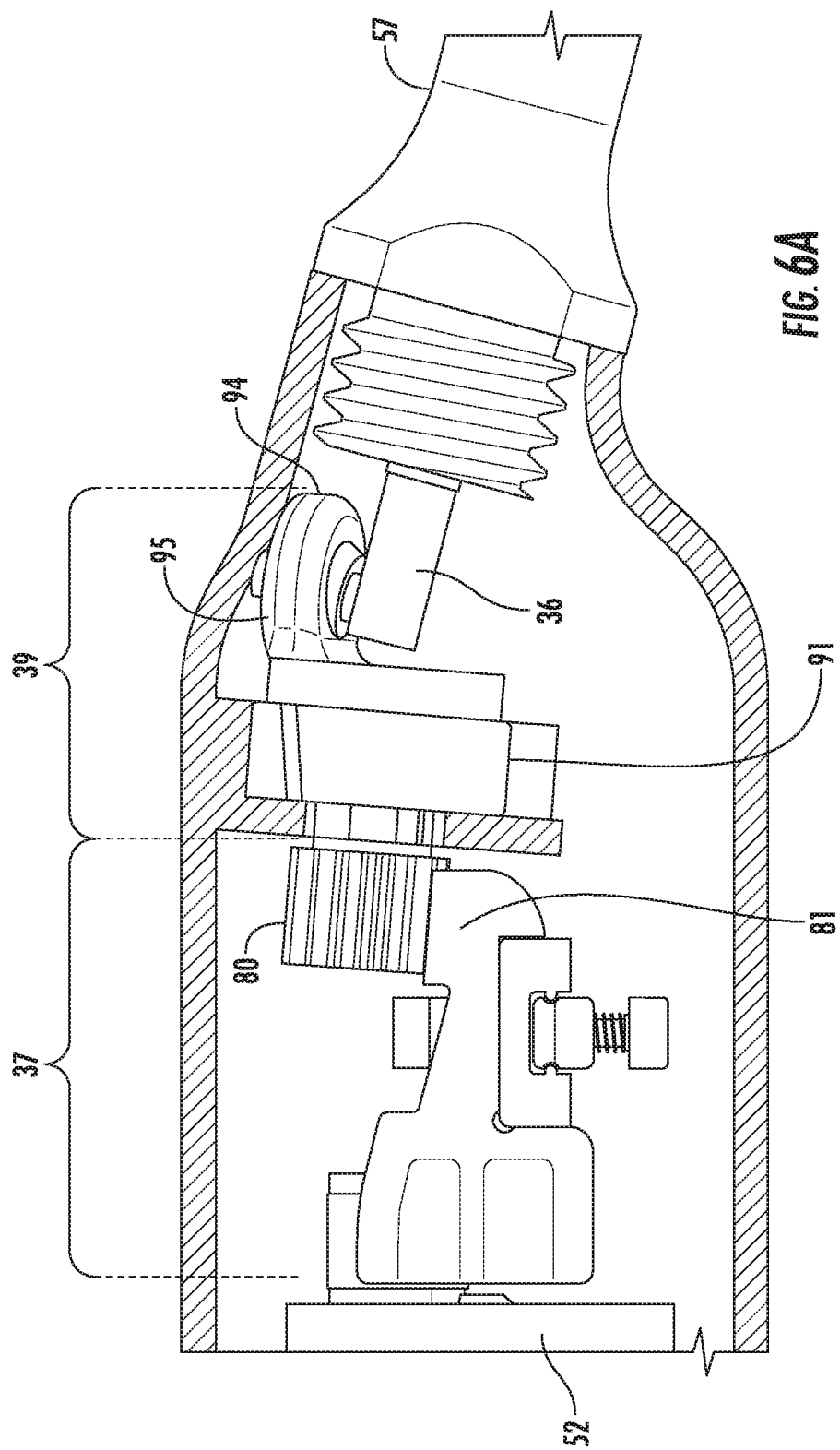

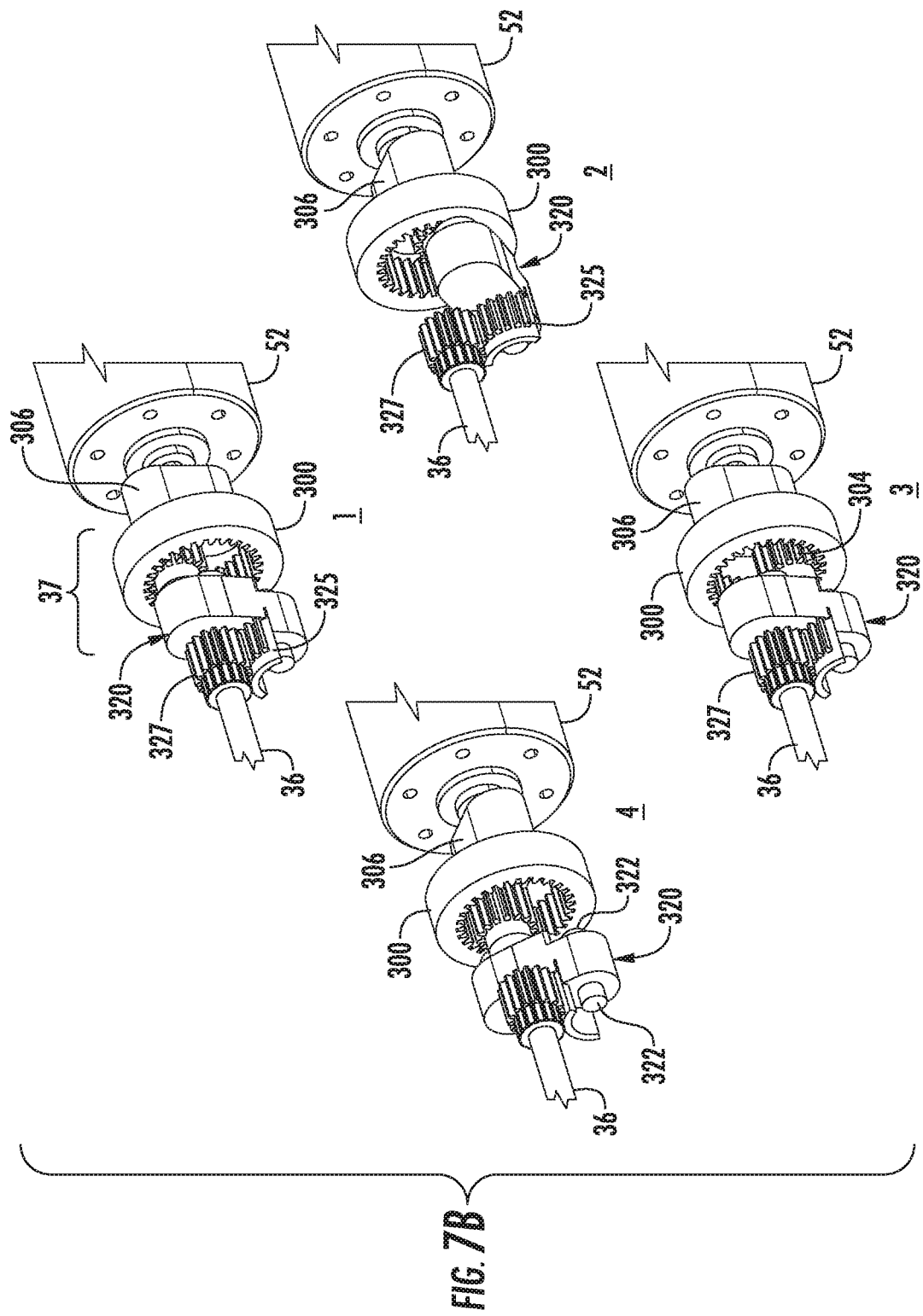

ROTARY OSCILLATING/RECIPROCATING SURGICAL TOOL

PRIORITY CLAIM

In accordance with 37 C.F.R. 1.76, a claim of priority is included in an Application Data Sheet filed concurrently herewith. Accordingly, the present invention claims priority to U.S. Provisional Patent Application No. 62/575,775, entitled "ROTARY OSCILLATING/RECIPROCATING TOOL", filed Oct. 23, 2017. The contents of the above referenced application are incorporated herein by reference.

FIELD OF THE INVENTION

The present invention relates to a powered surgical tool with a cutter adapted to modify tissue such as bone, cartilage and discs. The tool effects both rotary oscillation and longitudinal reciprocation of the cutter.

BACKGROUND OF THE INVENTION

The prior art has provided surgical tools having a rotary cutter adapted to modify tissue, such as bone, cartilage and discs in a patient. Such tools, though, present a problem if the cutter encounters fibrous tissue, such as muscle and nerves. Such fibrous tissue can wrap around the cutter and be damaged thereby. The prior art has also provided oscillating rotary tools for such surgical procedures, but the mechanisms used to effect oscillation of the cutter during its rotation do not operate smoothly due to the mechanisms used to effect oscillation. An advance in such oscillating tools is represented by our co-pending applications: U.S. Non-Provisional patent application Ser. No. 13/469,665, entitled "Rotary Oscillating Bone, Cartilage, and Disk Removal Tool Assembly, filed May 11, 2012; US International Application No. PCT/US2013/037071, entitled "Rotary Oscillating Bone, Cartilage, and Disk Removal Tool Assembly", filed Apr. 18, 2013; U.S. Non-Provisional patent application Ser. No. 13/647,101, entitled "Cutting Tool for Bone, Cartilage, and Disk Removal", filed Oct. 8, 2012 and now issued U.S. Pat. No. 9,232,953, issued on Jan. 12, 2016; US International Application No. PCT/US2013/063182, entitled "Cutting Tool for Bone, Cartilage, and Disk Removal", filed Oct. 3, 2013; U.S. Provisional Patent Application No. 62/460,481, entitled "Surgical Rotary Tool", filed Feb. 17, 2017; U.S. Non-Provisional patent application Ser. No. 15/895,352, entitled "Surgery Rotary Tool", filed Feb. 13, 2018; U.S. Provisional Patent Application No. 62/423,624, entitled "Rotary Oscillating Surgical Tool", filed Nov. 17, 2016; U.S. Non-Provisional application Ser. No. 15/814,891, entitled "Rotary Oscillating Surgical Tool", filed Nov. 16, 2017; U.S. Provisional Patent Application No. 62/423,651, entitled "Robotic Surgical System", filed Nov. 17, 2016; U.S. Provisional Patent Application No. 62/423,677, entitled "Robotic Surgical System", filed Nov. 17, 2016; and U.S. Non-Provisional patent application Ser. No. 15/816,861, entitled "Robotic Surgical System and Method", filed Nov. 17, 2017. The contents of each of the above referenced applications are herein incorporated by reference in their entirety.

Such tools are typically small and lightweight, with little room for drive mechanisms. They tend to operate at high cutting speeds for cutting efficiency and control by a surgeon. Oscillations are on the order of 10,000 oscillations per minute (5,000 orbits per minute). Reciprocation rate is preferably the same. An oscillation is movement of the cutter from one rotational position extreme to its other rotational extreme. Reciprocation is movement of the cutter from one linear movement position extreme to its other linear movement extreme. The cutter configuration and material being removed will determine cutter speed. Because of the high speed and need for precision placement and cutting, the tools need to be smooth in operation with little vibration.

SUMMARY OF THE INVENTION

According to one embodiment of the present invention, a surgical tool is provided with a housing, a cutter support shaft that is operably connected to a motor to effect oscillating rotation of the shaft, and a drive transmission configured between the motor and the shaft to effect oscillating rotary movement and simultaneous linear reciprocating movement of the shaft and cutter mounted to the shaft.

It is an objective of the present invention to provide an oscillation/reciprocation effecting drive transmission that utilizes a first driver to effect rotary oscillation of a cutter and to simultaneously effect driving of a second driver that is operable to add longitudinal reciprocating movement to the cutter.

It is yet another objective of the present invention to provide an oscillation/reciprocation effecting drive transmission that utilizes a rack and pinion gear arrangement to effect driving connection between the first and second drivers.

It is a still further objective of the present invention to provide a reciprocation effecting driver coupled to the oscillation effecting driver to effect simultaneous longitudinal reciprocation of the cutter shaft while it oscillates.

It is yet another objective of the present invention to provide a drive transmission that is simple in construction.

Other objects and advantages of this invention will become apparent from the following description taken in conjunction with any accompanying drawings wherein are set forth, by way of illustration and example, certain embodiments of this invention. Any drawings contained herein constitute a part of this specification, include exemplary embodiments of the present invention, and illustrate various objects and features thereof.

BRIEF DESCRIPTION OF THE FIGURES

FIG. 1 is a perspective view of the surgical tissue removal tool;

FIG. 2 is a cutaway fragmentary perspective view of the surgical tool of FIG. 1;

FIGS. 6A-6C illustrate various rotary positions of components of the second driver in the surgical tool that effect reciprocating movement of the cutting tool;

FIGS. 7A1-7A9 illustrate a Cardan type first driver of the transmission;

FIGS. 7B1-7B4 illustrate the Cardan drive of FIG. 7A1-7A9, and also include the output of the first driver and the input of the second driver;

FIG. 9 is a fragmentary side elevation view of a drive transmission as seen in FIG. 5;

DETAILED DESCRIPTION OF THE INVENTION

Figure 3:
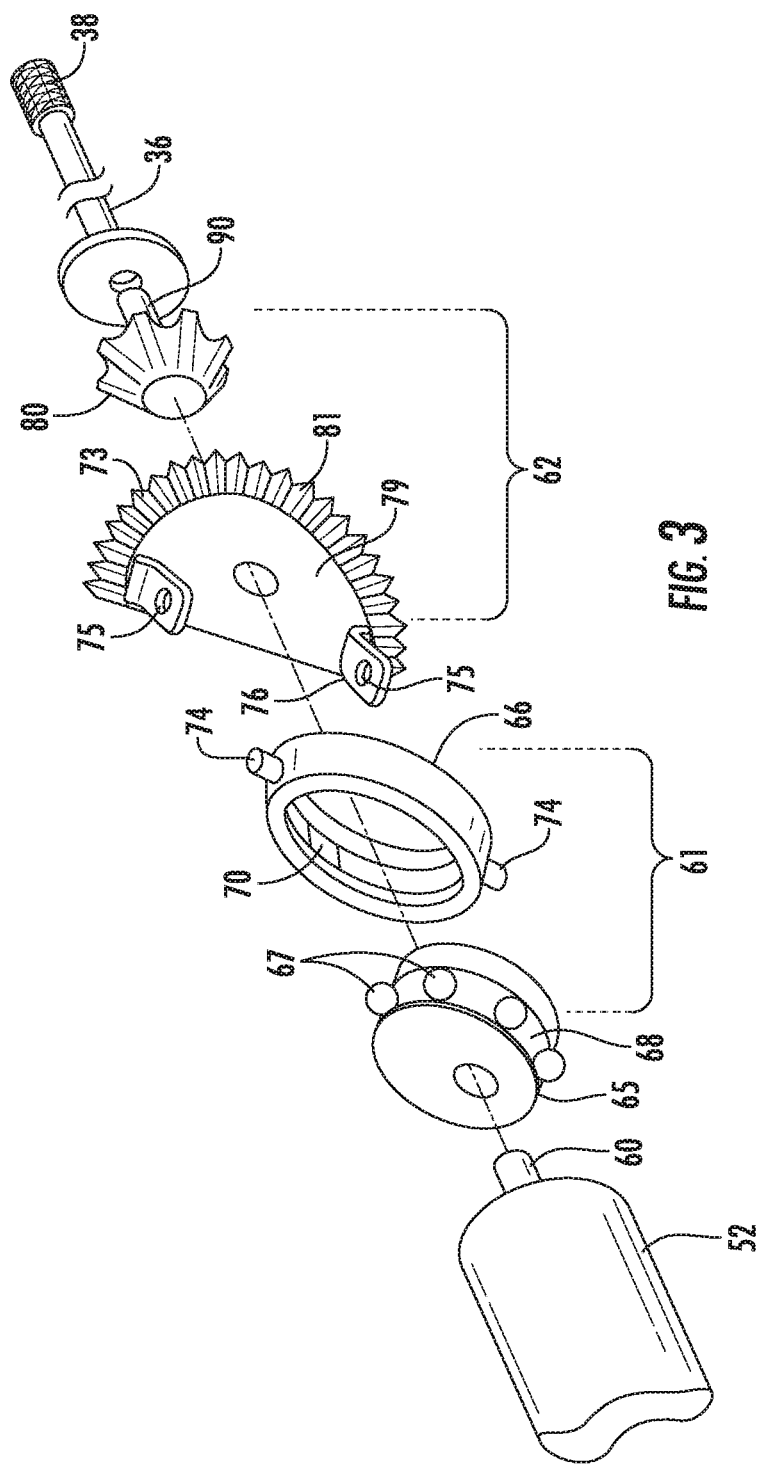
FIG. 3 is an exploded perspective view showing details of the internal parts of the surgical tool shown in FIG. 1.

The reference numeral 30 designates, generally, a rotary oscillating and reciprocating surgical tool useful, particularly, in the modification and/or removal of hard tissue such as bone, cartilage and disc material. The surgical tool 30 is illustrated as a handheld tool with a housing 32 providing a handle 34 for manually gripping the tool 30 for use during a surgical procedure. While one shape and style of handle 34 is illustrated, any suitable shape and style of handle can be provided. For example, a right angle pistol grip may be added. It is also to be understood that the handle 34 can be reconfigured from a handheld shape to a configuration for mounting the tool 30 to a surgical robot such as a 6 or 7 axis robot, such as those made by KUKA®. Additionally, the housing may have a narrow front portion for a smaller pencil-like "precision grip", while the larger remaining portion is sized to balance in the user's hand, such as in the web area between the index finger and thumb, for allowing better control with less fatigue.

The tool 30 can be used in surgical operations such as spinal surgery, wherein tissue, such as bone, cartilage and disc material that is preferably of a non-fibrous tissue type, may be modified or removed, such as from the spine of a patient. The tool 30 has an output shaft 36, which is driven to rotate in an oscillating manner of two alternate directions about the longitudinal axis of the shaft 36 by a drive transmission 35 that has two driver components, including a shaft 36 oscillation effecting first driver 37. Shaft 36 is provided with a cutting tool 38 positioned and secured to a distal end portion of the shaft 36. The cutting tool 38 is driven to rotate in alternate directions (oscillation) like the shaft 36, with a limited range of angular displacement of rotation, for example, between about 90° and about 180°. It has been found that such oscillatory rotation is effective in cutting or modifying hard tissue like bone, cartilage and portions of discs. It has also been found that this oscillatory rotation reduces the risk of damage to fibrous tissue such as muscle and nerve.

The transmission 35 is also preferably provided with a shaft 36 reciprocation effecting second driver 39 coupled to the first driver 37 to simultaneously effect reciprocating motion of the shaft 36 and cutting tool 38 while they are oscillating. The reciprocation driver 39 uses the oscillating output of the first driver 37 to add the reciprocating motion to the shaft 36 and cutting tool 38. Reciprocating movement is parallel to the longitudinal axis of the shaft 36. The first driver 37 is upstream operationally of the second driver 39.

The tool 30 can receive energy for its operations from an external supply, such as a direct current power supply cord 40. A power control switch 42 can be provided on the housing 32 for controlling the operation of the tool 30, such as in an ON and OFF manner and/or in a variable speed manner. A light source 44 may also be provided on the housing 32 for illuminating the surgical site. Such a light source may be a light emitting diode (LED), which can be powered directly or indirectly by energy from cord 40. Energy can also be provided by a battery 46 or other energy storage device.

FIG. 2 illustrates internal components of the tool 30. An energy source can be provided by a battery supply 46 mounted in the housing 32. The battery supply 46 can be charged by the power cord 40. Electronics 48 are provided in the housing 32 for controlling the operation of the tool 30. A plurality of indicator lamps 50 may also be provided on the housing 32, and can be LEDs for indicating operational characteristics of the tool 30, such as the state of charge of the battery supply 46. Alternately, the batteries 46 can be eliminated in favor of the cord 40 being connected to a source of electrical energy. Preferably, the power supply is low voltage, e.g., 12 volts, i.e., low enough to not present a danger to the operator and/or patient. Additionally, the motor 52 can be powered by compressed air, a vacuum, or any other suitable source of energy that would, on demand, effect rotation of a rotor portion of the motor 52 and hence shaft 36.

The motor 52 is suitably mounted in the housing 32, wherein a portion of the motor, a rotor (not shown), is free to rotate and ultimately drive the shaft 36. A portion of the motor 52 is fixed against rotation in the housing 32 as is known in the art; for example, a motor housing and/or stator. The motor 52 drives the shaft 36 through the transmission 35 and its drivers 37, 39. The first driver 37 is operable for converting continuous rotary motion from the motor 52 to rotary oscillation of the shaft 36. The second driver 39 is operable for converting continuous oscillation from the first driver 37 and continuous rotation of the motor 52, and adds continuous reciprocating longitudinal movement to the shaft 36. The shaft 36 is suitably mounted in the nose 57 of the housing 32, as in one or more bearings 59. Operationally, the first driver 37 is upstream of the second driver 39. The bearings 59 are configured to accommodate both rotary and linear movement of the shaft 36, and a suitable bearing is a journal bearing 59. The shaft 36 may be angled relative to the longitudinal axis of the housing 32, as depicted in FIG. 1, for ergonomics. Cooling fins, or a cooling fan, may be attached to or near the motor 52 for cooling the motor and/or the tool 30.

FIGS. 3-18 illustrate different forms of drivers 37 and 39.

Figure 4:
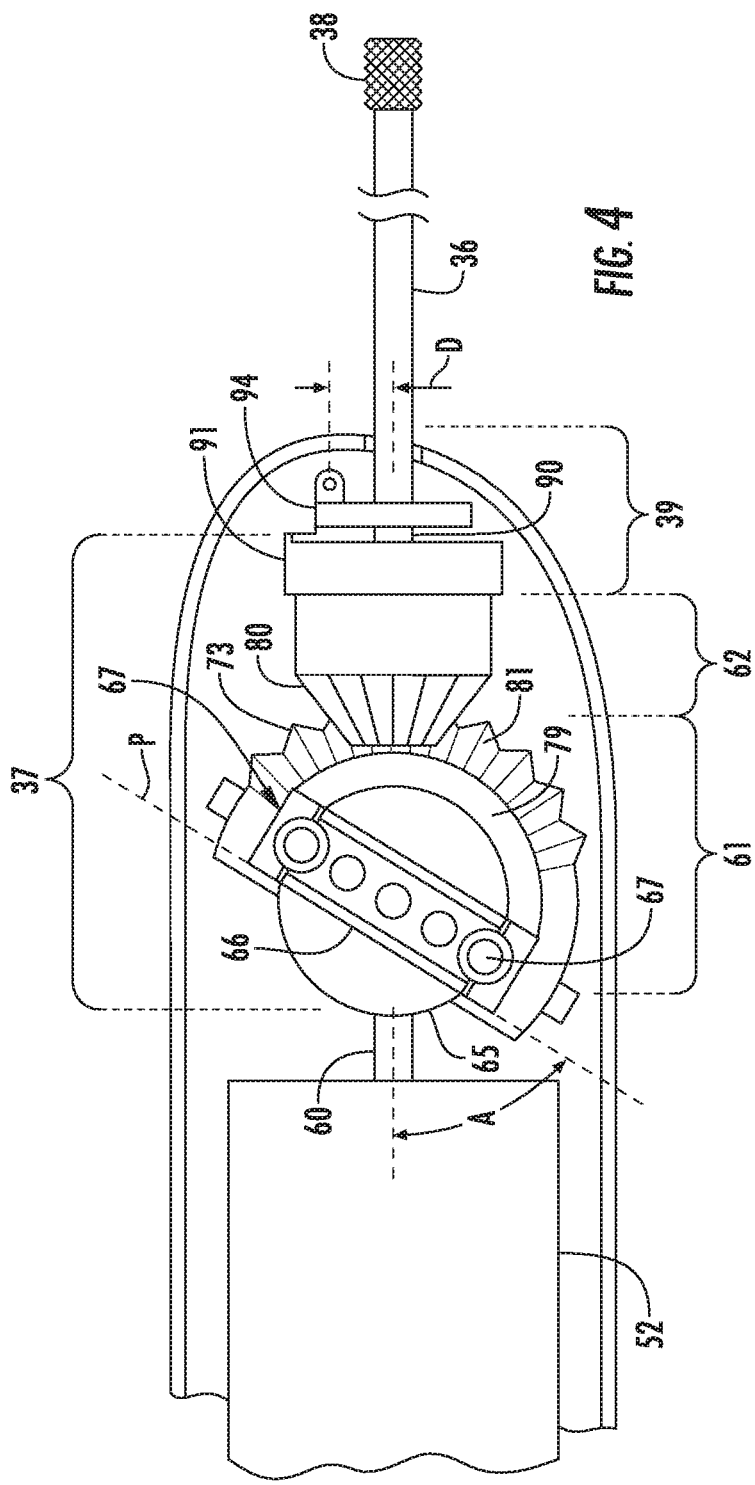
FIG. 4 is a top plan view of the details of the internal parts of the surgical tool shown in FIG. 1.
Figure 5:
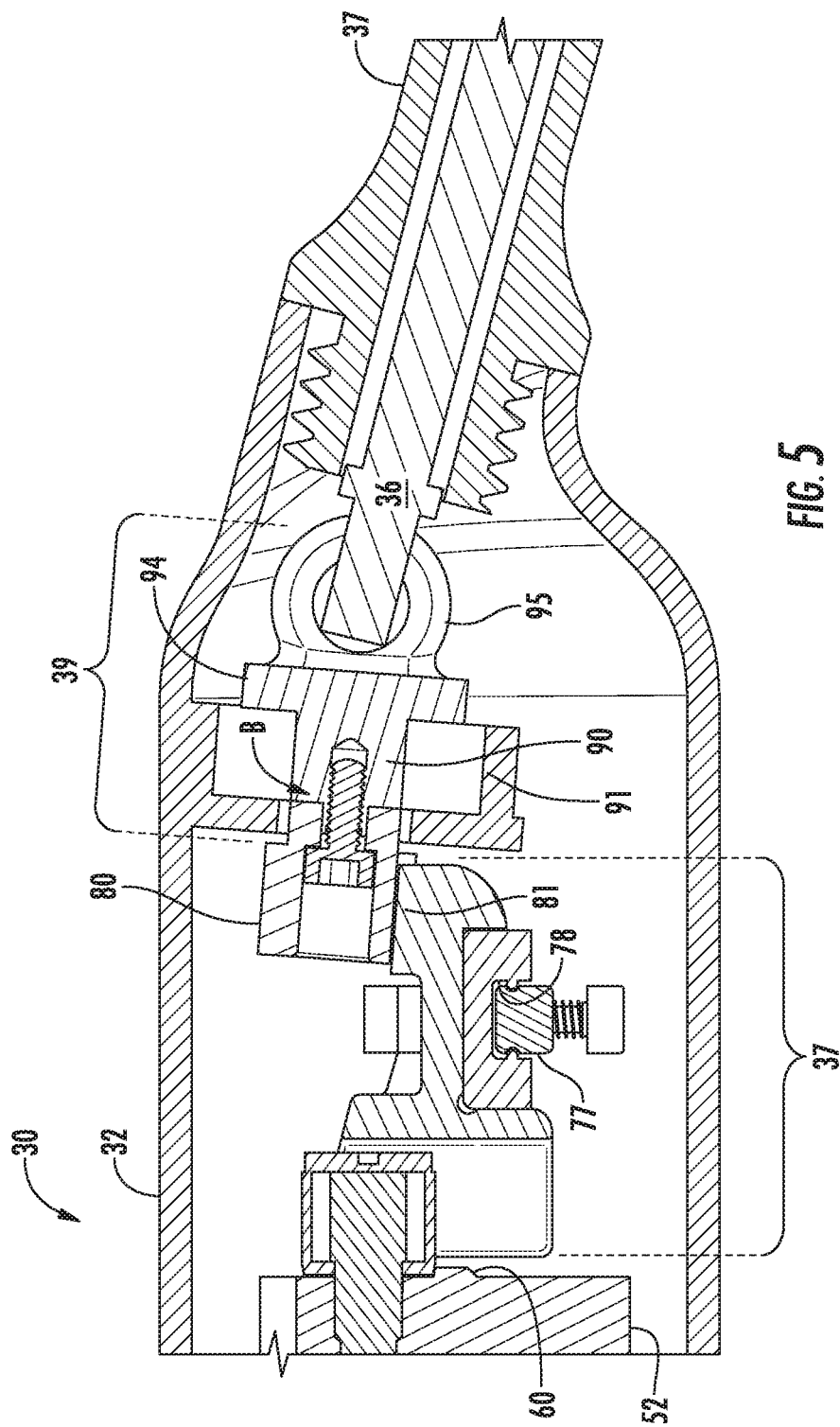
FIG. 5 is a fragmentary side view showing two drivers in the surgical tool shown in FIG. 1.

The first driver 37, as best seen in FIGS. 3-4, is positioned in the housing 32 and operably couples the second driver 39, and hence shaft 36, to the motor 52, and is operable to convert the continuous rotary motion of the shaft 60 of the motor 52 to oscillating rotary motion of the shaft 36. By oscillating rotary motion, it is meant that the shaft 36 will rotate a portion of a complete revolution first in one rotation direction and then in the other rotation direction, first counterclockwise, then clockwise, then counterclockwise again and so on. To effect this movement, the transmission 35 comprises the two driver components 37, 39. The first driver 37 is coupled to the motor 52 and is operable to convert the rotary motion of the shaft 60 of the motor 52 to oscillating rotary motion of the shaft 36; and the second driver 39 is coupled to the first driver 37 and is operable to convert that oscillating motion to reciprocating linear motion while maintaining the oscillating motion.

In the illustrated embodiment, the first transmission driver 37 includes a ball bearing having an inner race 65, an outer race 66 and a plurality of bearing balls 67 contained in the races 65, 66. The inner race 65 is secured to the motor shaft 60 for rotation thereby about the central axis of the motor shaft 60. In the illustrated embodiment, the inner race 65 is in the form of a sphere, with a groove 68 therein, and sized to receive and retain the balls 67 therein. The outer race 66 is in the form of a ring, having a groove 70 recessed in the inner surface thereof, and sized to receive and retain the balls 67 therein. The grooves 68, 70 open toward one another and are positioned in a plane P that is set at an angle A relative to the longitudinal axis of the motor shaft 60. The angle A is the smallest angle between the plane P and shaft axis since the angle of the plane P relative to the shaft axis changes depending on the position of measurement taking. The angle A is in the range of between about 30° and about 80°.

The outer race 66 is coupled to an oscillating connector 73, as for example with a pair of opposed pivot pins 74 projecting outwardly from the outer race 66 and each being received in a respective bore 75 in a respective ear 76. The connector 73 is restrained in movement to a plane. In one example, a guide 77 (FIG. 5) is secured to the housing 32. The guide 77 is curved, and is received in a similarly curved slot 78 cooperating with the driver 37. Thus, the outer race 66 can only move in an oscillating manner, as can the connector 73. Another means to mount the connector 73 is with a pivot pin secured to the housing 32 and extending through a web portion 79 of the connector 73, which allows the connector 73 to rotate in an oscillating manner. The illustrated connector 73 has a curved gear rack portion 81 coupled to the web 79 and carried thereby. A gear or gear segment, herein a gear 80, such as a bevel gear, engages the rack portion 81 of the driver 73 and itself is driven in an oscillating manner by rotation of the inner race 65 as driven by the motor 52. The gear 80 is coupled to the shaft 36 by the second driver 39 to effect driving of the shaft 36 in an oscillating manner.

The angle A determines the degree of rotation of the gear 80, and the rotational speed of the motor 52 determines the oscillation rate of the gear 80.

Figure 6B:
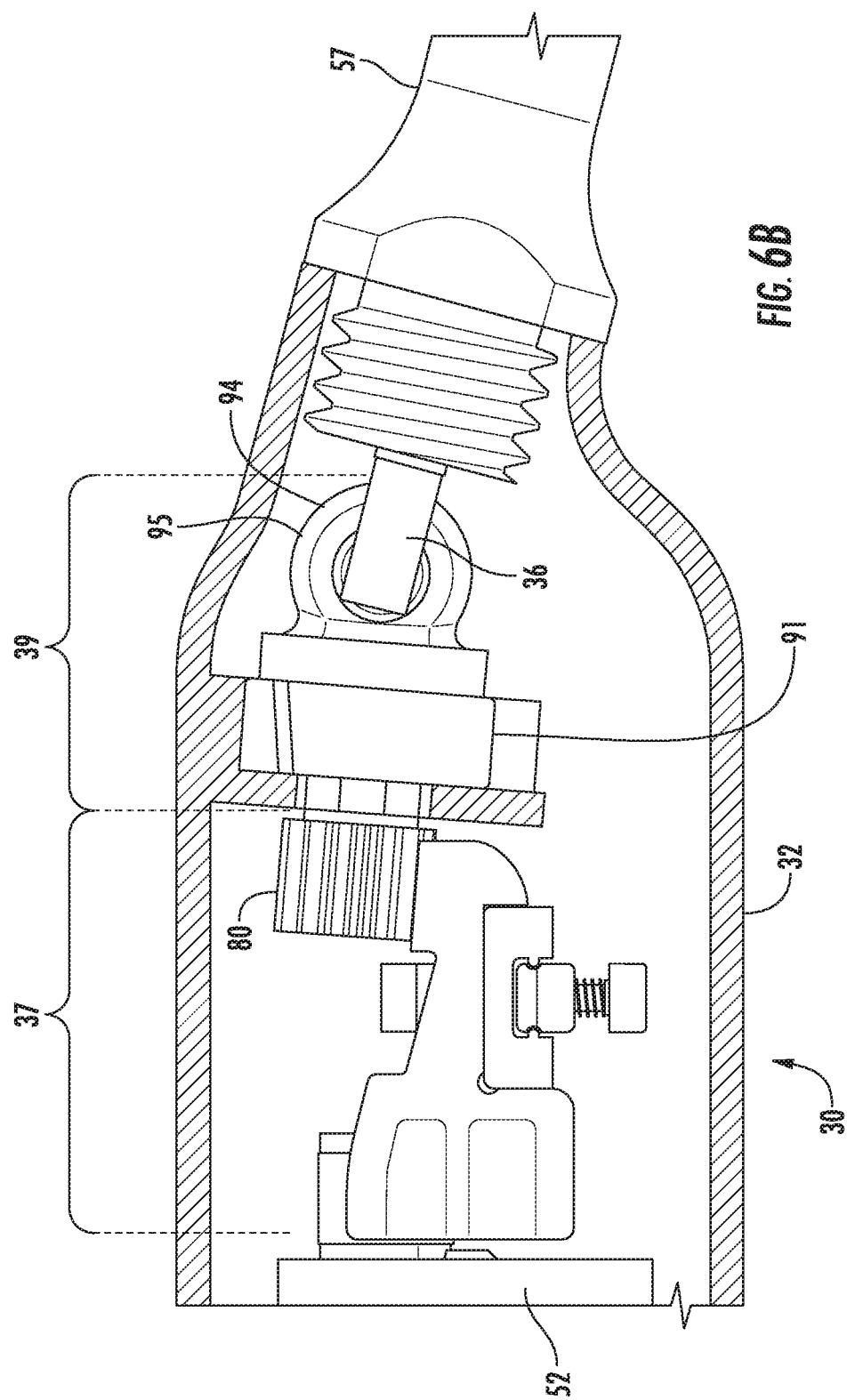
Figure 6C:
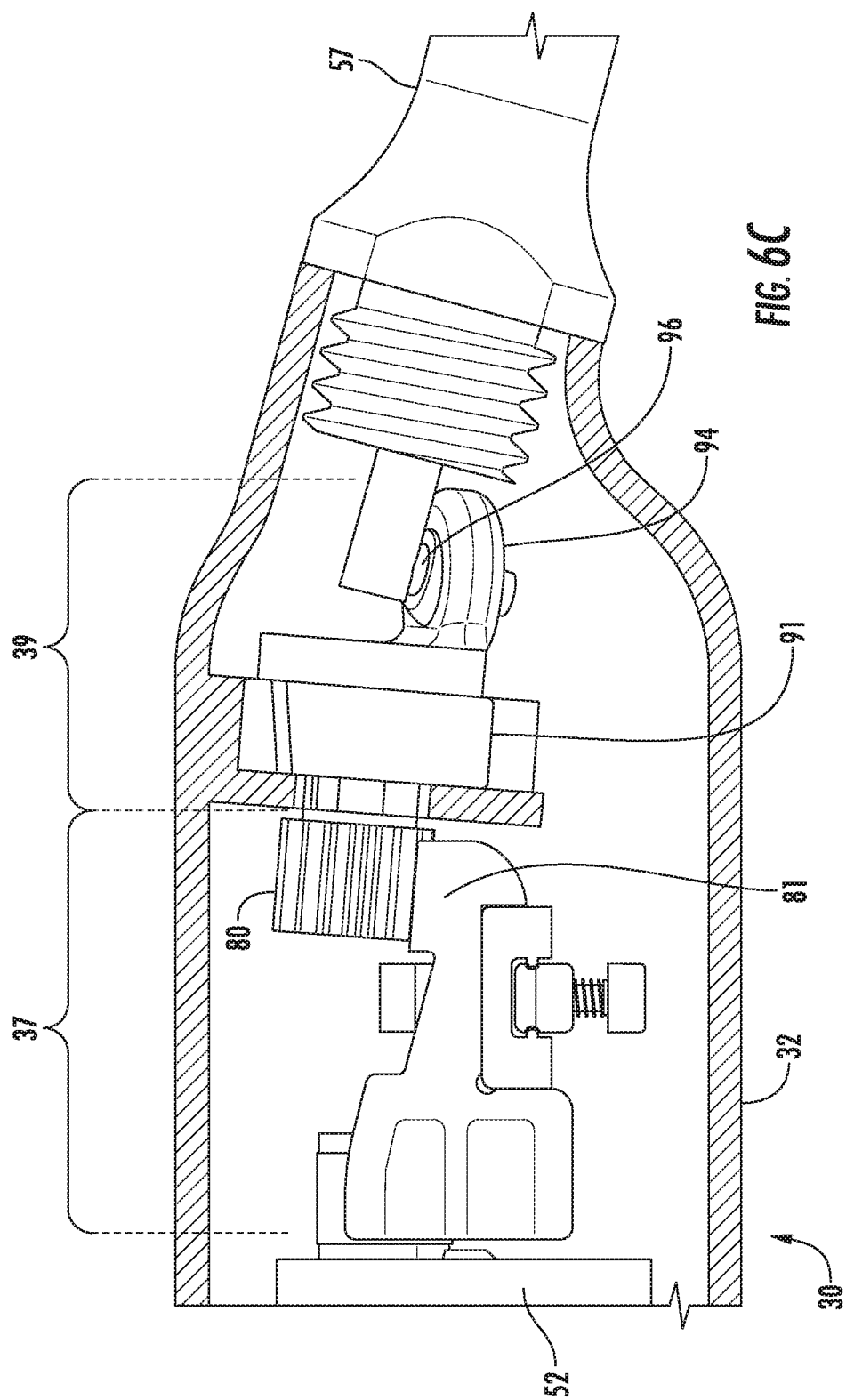

The gear 80 is part of the second driver 39, and is coupled to the shaft 36 to effect motion of the shaft 36 and associated cutting tool 38 as described herein. As shown, the gear 80 is fixed to a shaft 90 that is rotatably mounted to the housing 32 via a suitable bearing 91 fixed in position in the housing 32. The gear 80 is maintained in driving engagement with the rack 81, which oscillates along a curved path during operation of the motor 52. The shaft 36 is secured to a reciprocation effecting joint 94 in a manner allowing part of the joint 94 to pivot during rotation of the joint 94 and shaft 36. See FIGS. 6A-6C. Oscillation of the shaft 90 and the joint 94 effects oscillation of the shaft 36. The longitudinal axis of the shaft 90 intersects the longitudinal axis of the shaft 36, FIGS. 4, 5, and the axes are positioned at an angle B relative to one another. By being positioned at an angle B, which is preferably in the range of between about 5° and about 45°, the shaft 36, during oscillating rotation, will move longitudinally in two directions, effecting reciprocal movement of the shaft 36 and cutting tool 38 during their oscillating movement. To allow for both oscillation and reciprocation, the shaft 36 can be mounted in one or more journal bearings 59 fixed in position in the housing 32 and/or nose 57. The joint 94 acts as a wobble plate because of the angle B. Additionally, to effect the reciprocating movement, the shaft 36 is secured to the joint 94 at a position offset radially outwardly from the center of its rotation, the center of the shaft 90, FIGS. 4, 6A. This offset dimension D also determines the amount of reciprocating movement of the shaft 36. In a preferred embodiment, the joint 94 oscillates about 180° and starts at a rotational position, where the shaft 36 is at its most retractable position, and ends at its most extendable position. The joint 94, as shown, includes a tab 95 on which is mounted a ball or spherical bearing 96, see FIG. 8. The shaft 36 is coupled to the bearing 96 as with a pin 98. FIGS. 6A-6C illustrate the joint 94 in three different rotary positions and three different reciprocating positions. In FIG. 6A, the shaft is in its most extended reciprocating position. FIG. 6B shows the shaft 36 in an intermediate extended position. FIG. 6C shows the shaft 36 in its most retracted reciprocating position.

Figure 10:
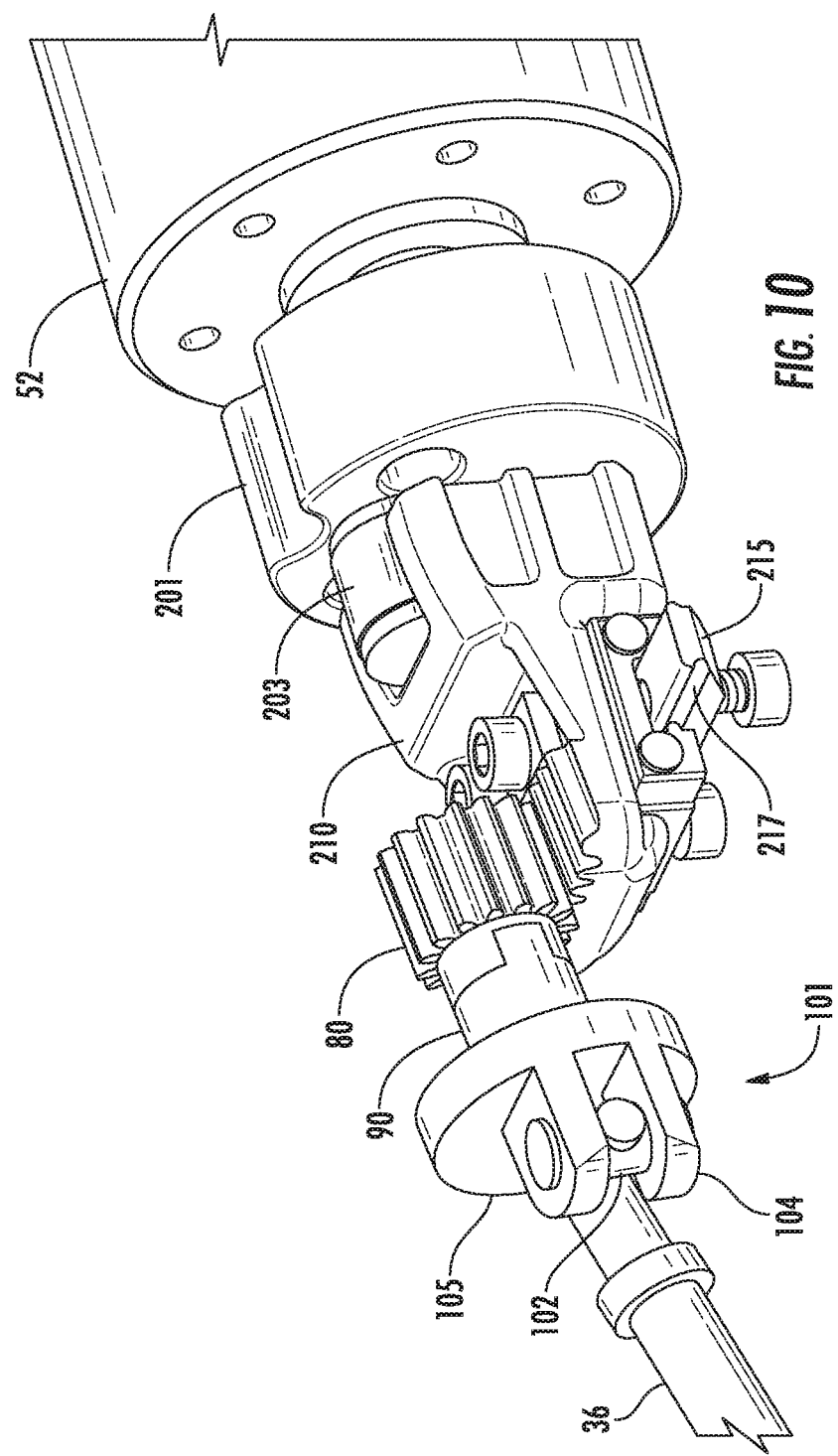
FIG. 10 is a fragmentary perspective view of a drive transmission similar to that shown in FIG. 8.

FIG. 10 illustrates another embodiment of connecting the shaft 36 to the second driver 39. The joint 101 is used instead of the joint 94. A pivot pin 102 is mounted for rotation in a clevis 104, which in turn is mounted to a crank member 105. The crank member 105 is mounted to a shaft 90, which is rotatably mounted in the bearing 91 as described above. The shaft 36 is secured to the pin 102. This form of joint 101 is similar in operation to the joint 94 described above.

Figure 11:
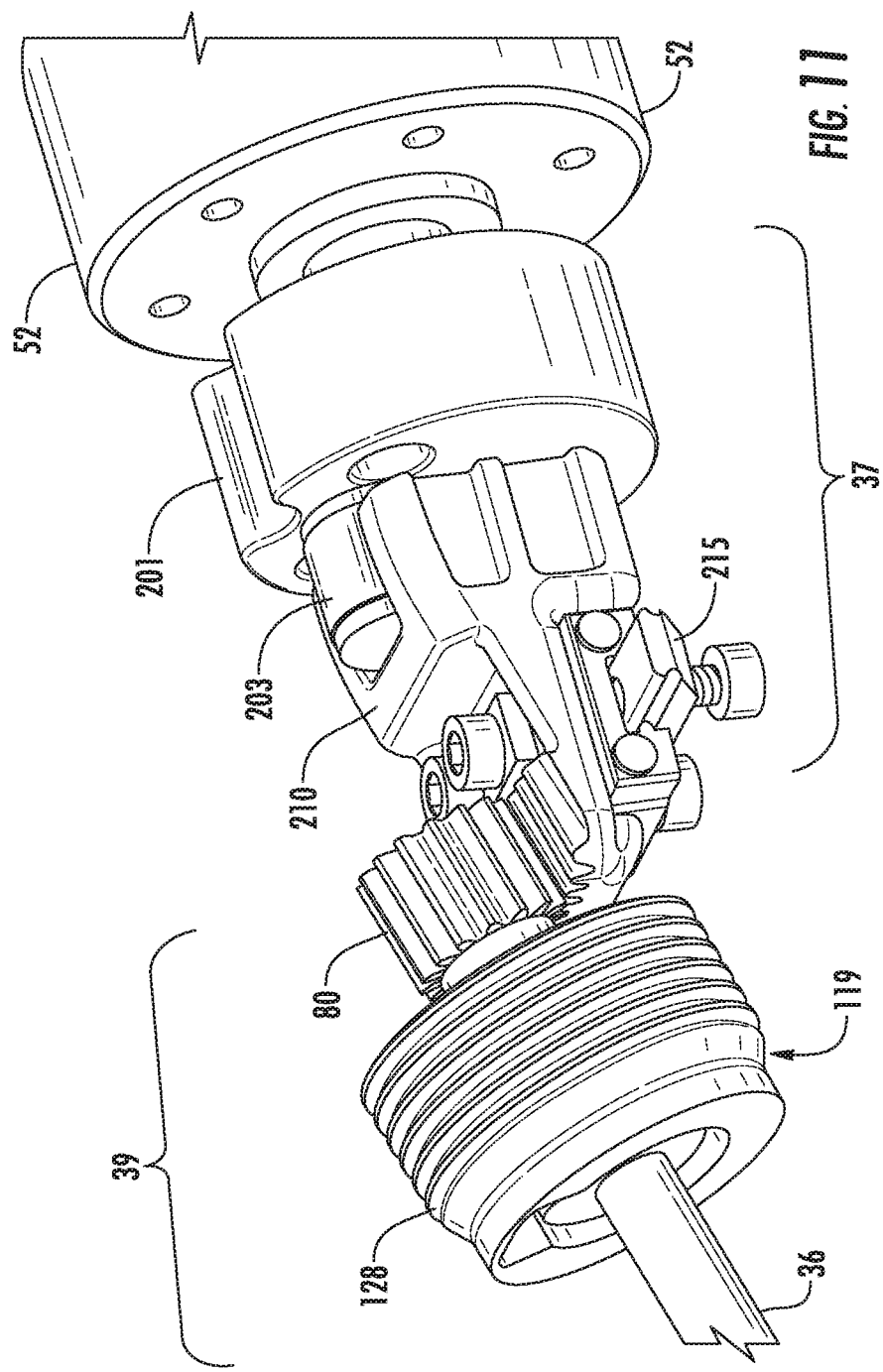
FIG. 11 is a fragmentary perspective view of another embodiment of a drive transmission similar to that shown in FIG. 8, but with an alternate second driver.
Figure 12:
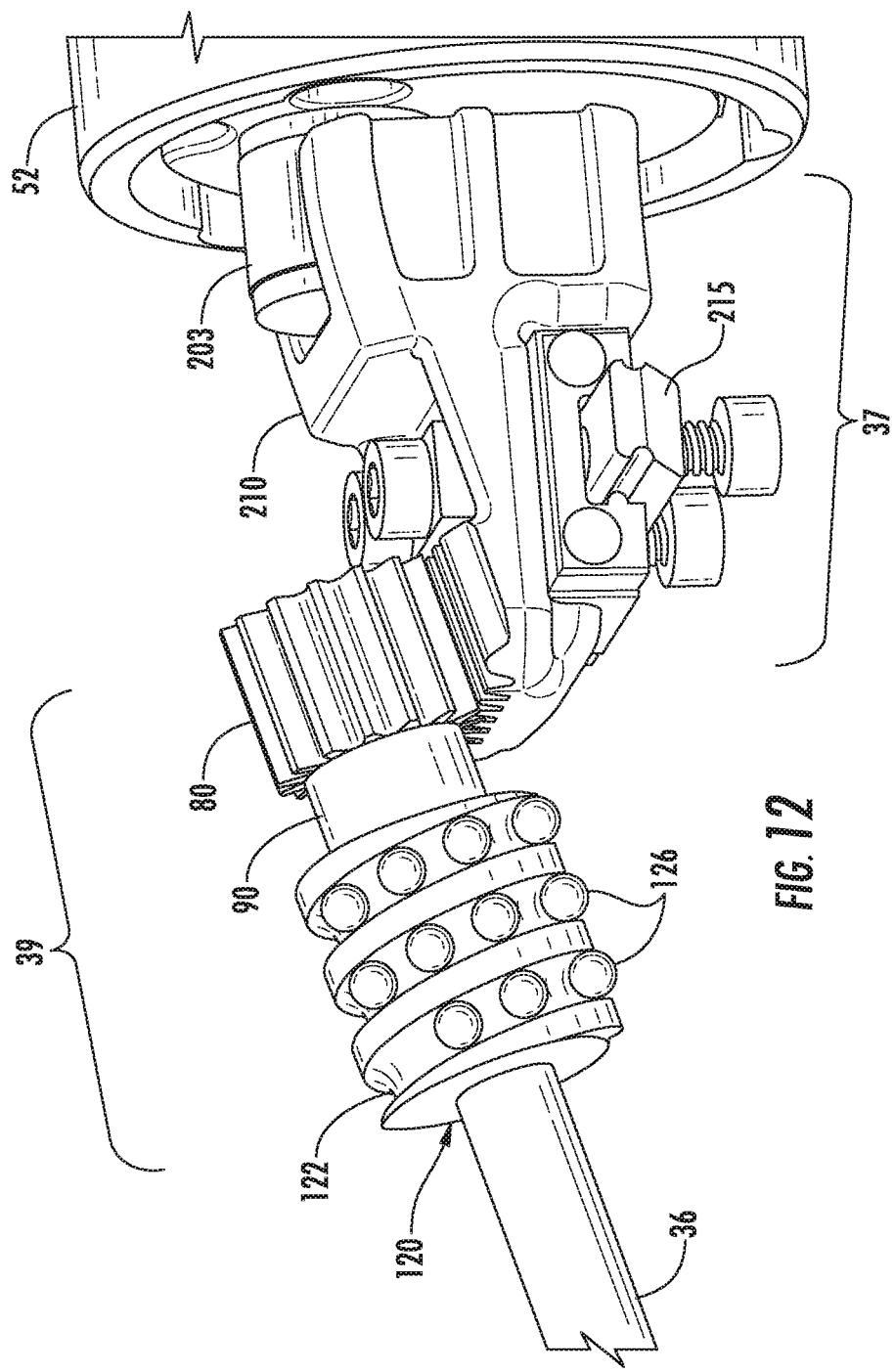
FIG. 12 is a fragmentary perspective view of a drive transmission showing details of parts in FIG. 11.
Figure 14:
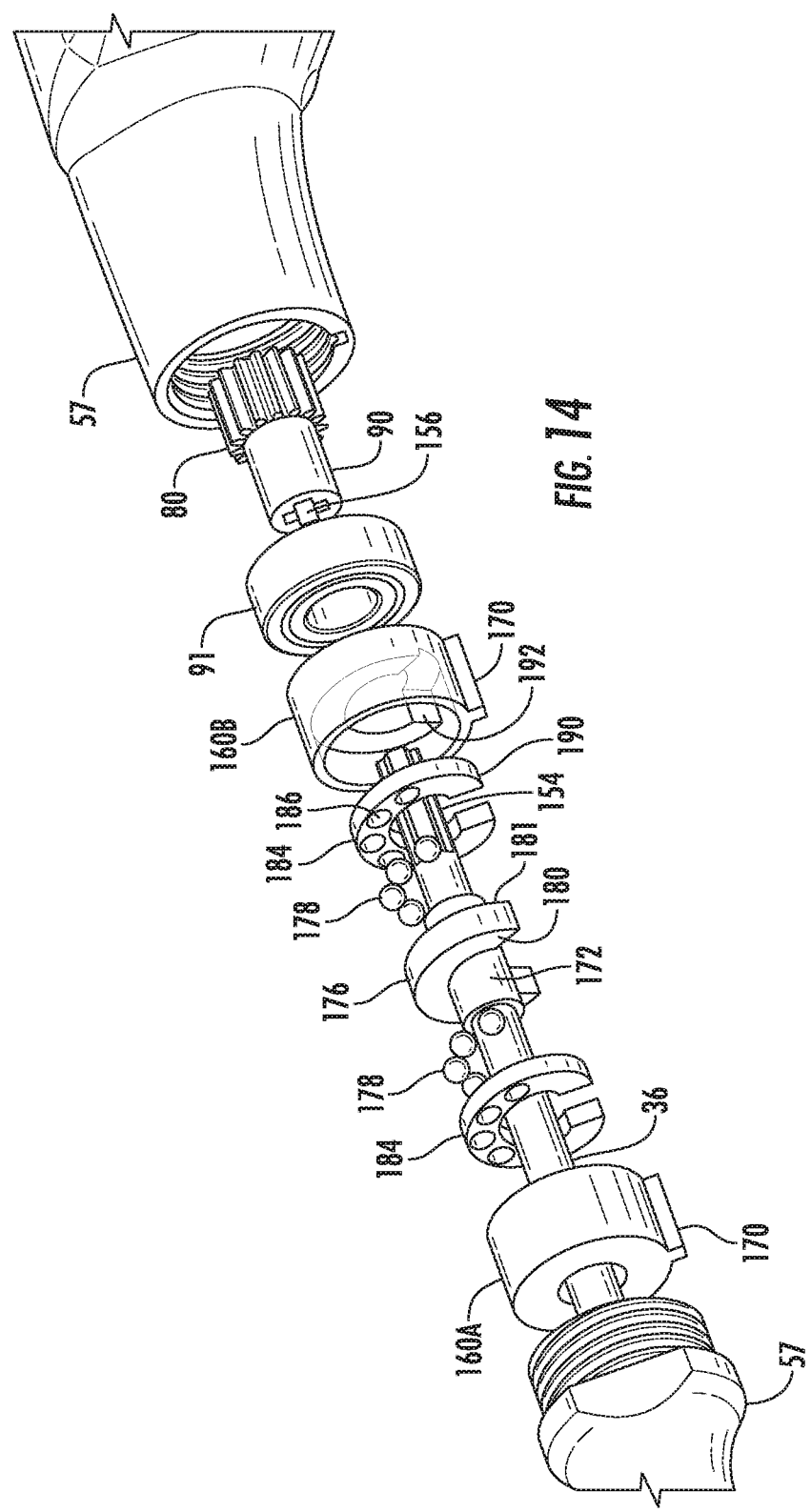
FIG. 14 is an exploded fragmentary perspective view of a portion of the drive transmission shown in FIG. 13.
Figure 15:
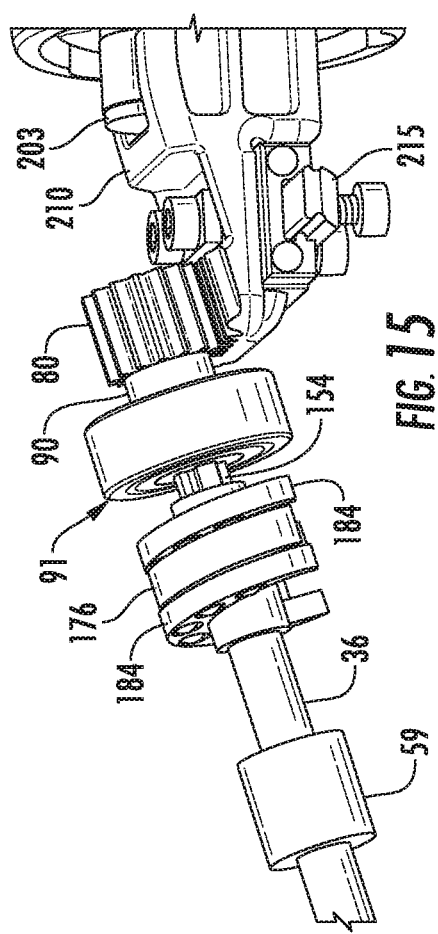
FIG. 15 is a fragmentary perspective view of portions of the drive transmission of FIG. 13.
Figure 16:
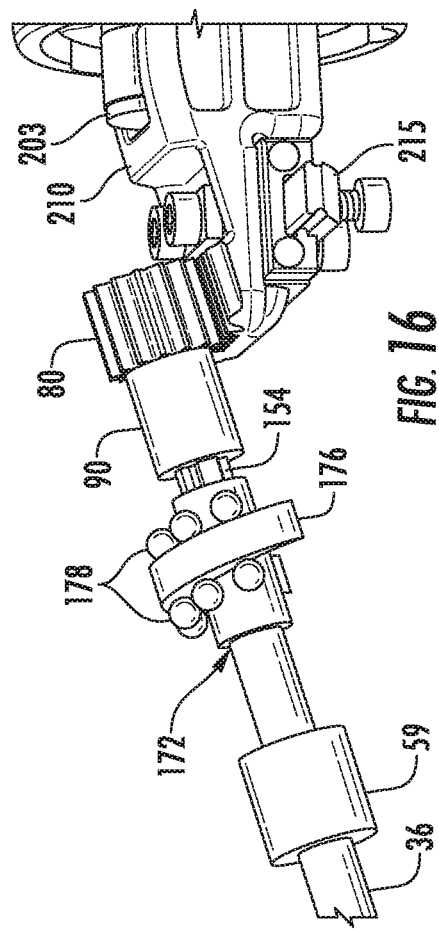
FIG. 16 is a fragmentary perspective view of portions of the drive transmission of FIG. 13.

FIGS. 11, 12 illustrate another embodiment of a second driver 39 that is operable to effect longitudinal reciprocating movement of the shaft 36. The shaft 36 is coupled to the shaft 90 for relative longitudinal movement therebetween, as for example by the use of a spline connection, as can be seen in FIG. 14. A helical bearing 119, for example like a ball screw, has an inner bearing race 120 secured to the shaft 36 for rotation therewith. The race 120 has an outwardly opening helical bearing groove 122. A plurality of bearing balls 126 are contained within the groove 122. The helical bearing 119 has an outer bearing race 128 mounted in the housing 32 or nose 57, and is fixed against movement relative thereto. The outer bearing race 128 has a helical groove (not shown) that opens inwardly and contains the bearing balls 126 therein. When the shaft 36 rotates in an oscillating manner, as effected by the first driver 37, the shaft 36 will move in a longitudinal reciprocating manner by cooperation between the inner and outer bearing races 120, 128, respectively, via the bearing balls 126. This forces the inner race 120, along with shaft 36, to move longitudinally in a reciprocating manner. The pitch of the groove 122 and degree of oscillation will determine the amount of reciprocation.

Figure 13:
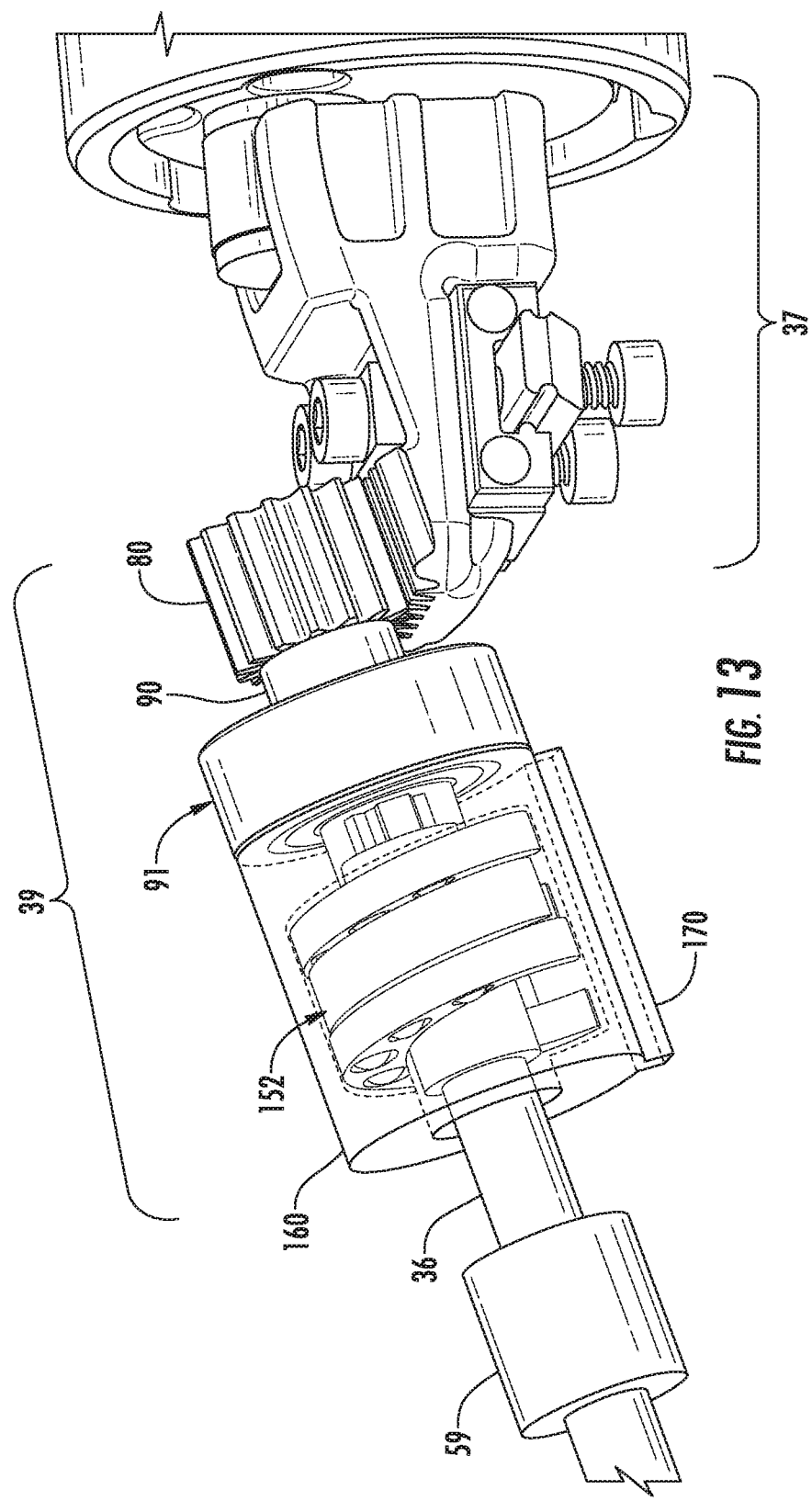
FIG. 13 is a fragmentary perspective view of another embodiment of a drive transmission.

FIGS. 13-16 illustrate a further embodiment of a second driver 39 that is operable to effect longitudinal reciprocating movement of the shaft 36. This embodiment uses a helical bearing 152 to effect longitudinal reciprocating movement of the shaft 36 while the shaft 36 is being rotationally oscillated by the first driver 37. As seen in FIG. 14, the shaft 36 has its proximal end 154 male splined, and is longitudinally movably received in a female splined socket 156 within the shaft 90. Thus, the shaft 36 can move both longitudinally and rotationally while being driven by the drivers 37, 39. The helical bearing 152 includes a split housing 160 having housing portions 160A and 160B. The housing 160 is mounted in the housing 32 and/or its nose 57 in a manner to prevent relative rotation therebetween. This can be accomplished, as seen in FIGS. 13, 14 by providing the housing 160 with a laterally projecting key 170. The bearing 152 has an inner race 172 secured to the shaft 36 and provides a radially projecting helically longitudinally extending flange 176. Bearing balls 178 are positioned on opposite faces 180, 181 of the flange 176. The bearing 152 is provided with a pair of outer races 184 that have a plurality of bearing ball receiving pockets 186 in the faces opposite the faces 180, 181 of the flange 176. The outer races 184 retain the bearing balls 178 in contact with their respective face 180 or 181. Rotation of the outer races 184 relative to the housing portions 160A and 160B is limited by stop faces 190 on the outer races 184, and stop faces 192 on the inside of the housing portions 160A and 160B.

Figure 8:
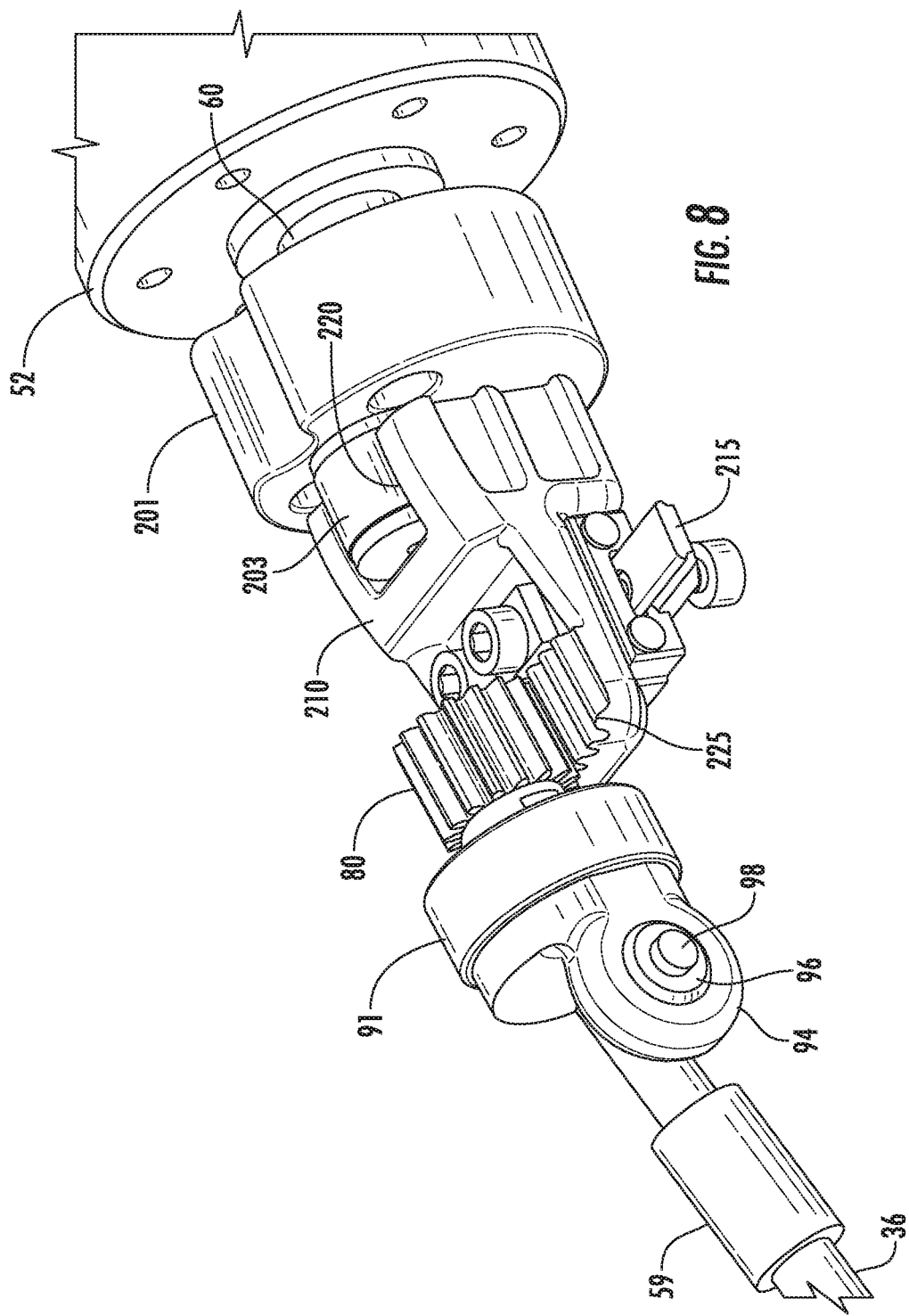
FIG. 8 is a fragmentary perspective view of one embodiment of a drive transmission.
Figure 9:
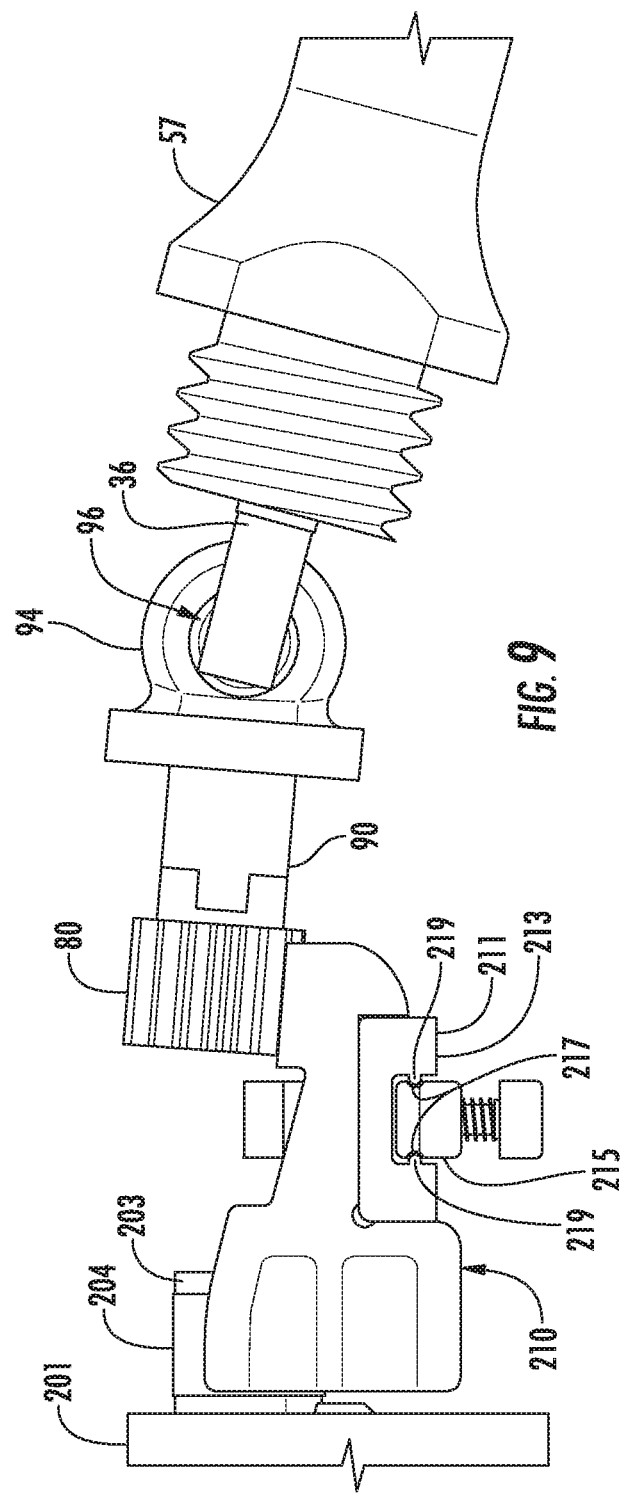

FIGS. 8, 9 illustrate a second embodiment of the first driver 37. It is similar to the driver 37 shown in FIGS. 5, 6A-6C. The motor 52 has a crank assembly 201 mounted on its output shaft 60. The crank assembly 201 includes a drive arm 203 that can include a wear resistant bearing member 204. The drive arm 203 is offset radially from the center of rotation of the crank assembly 201. Thus, rotation of the crank assembly 201 moves the drive arm 203 in a circular path. A follower assembly 210 is mounted in the housing 32 in a manner to restrict its movement in a plane laterally from side to side. As shown, a guide bed 211 is provided and includes a guide channel 213, which receives in it a guide rail 215. As shown, the guide rail 215 is coupled to the bed 211 to prevent their separation during movement. As illustrated, the guide rail 215 has a pair of opposed grooves 217, in each of which is received a respective guide rail 219 to provide guided restrained movement between the guide bed 211 and guide rail 215. The guide rail 215 is straight, thereby restricting movement of the follower assembly to linear movement in a plane. The drive arm 203 is received in a channel 220 with a close fit, whereupon revolving movement of the drive arm 203 will effect reciprocating lateral movement of the follower assembly 210. The follower assembly 120 is drivingly coupled to the second driver 39 in a manner to effect oscillating rotation of the shaft 36. As shown, a gear rack 225 is provided on the follower assembly 210 to mesh with the gear 80, whereby lateral movement of the follower assembly 210 effects oscillating rotation of the shaft 36, which, with operation of the second driver 39, will simultaneously effect reciprocating motion of the shaft 36.

Figure 7A:
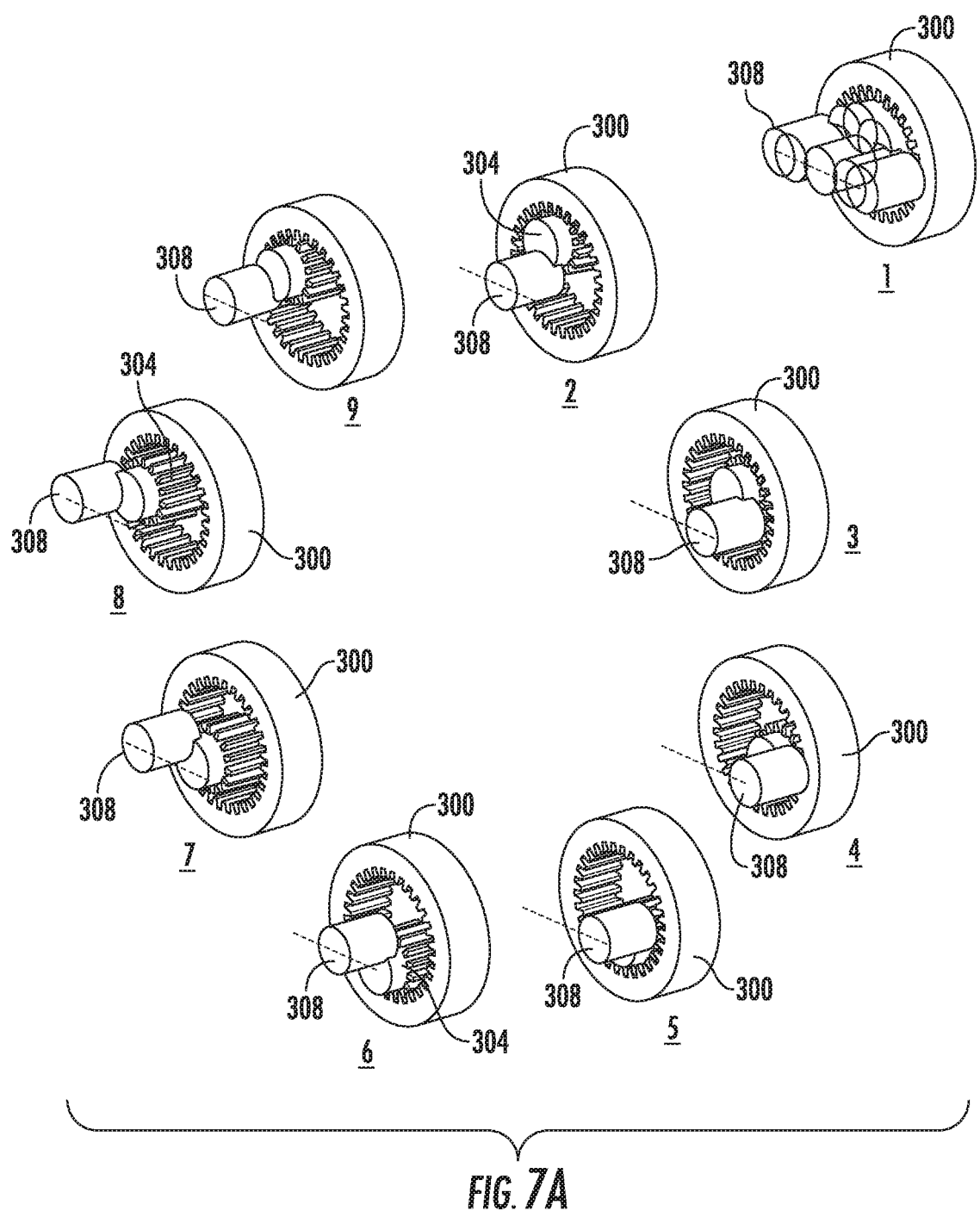
Figure 17:
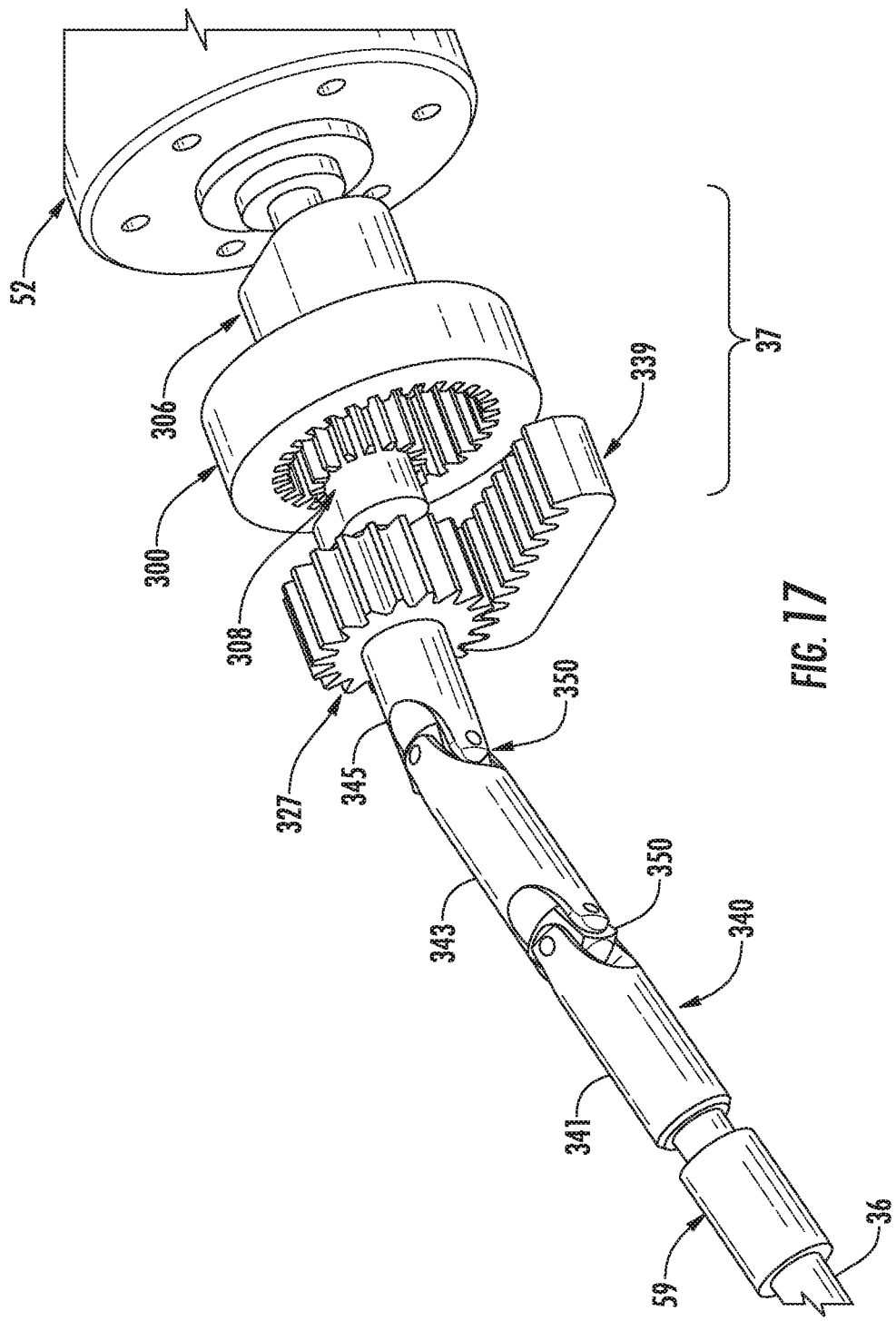
FIG. 17 is a fragmentary perspective view of portions of a still further embodiment of a drive transmission.
Figure 18A:
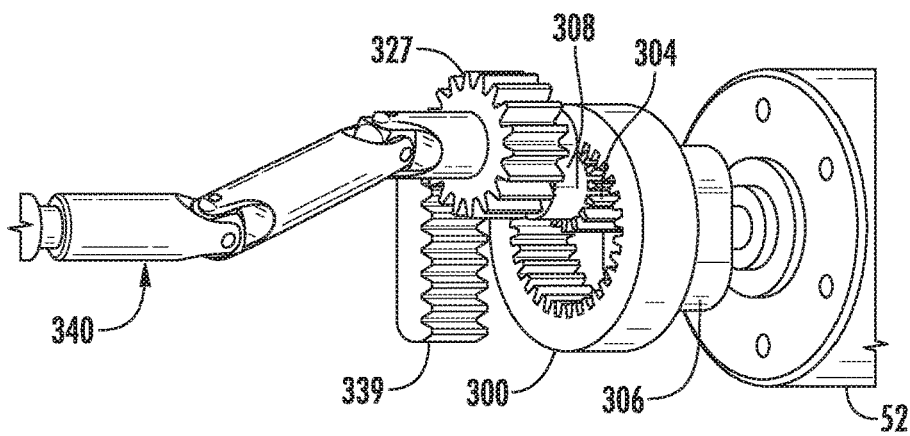
FIGS. 18A-18D are fragmentary perspective views of portions of the transmission of FIG. 17 showing sequential positions of portions of the second drive effecting reciprocating movement of a cutter shaft and associated cutter.
Figure 18B:
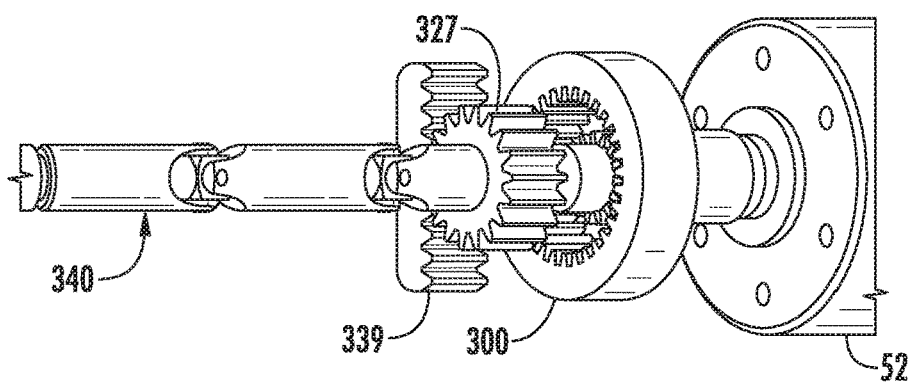
Figure 18C:
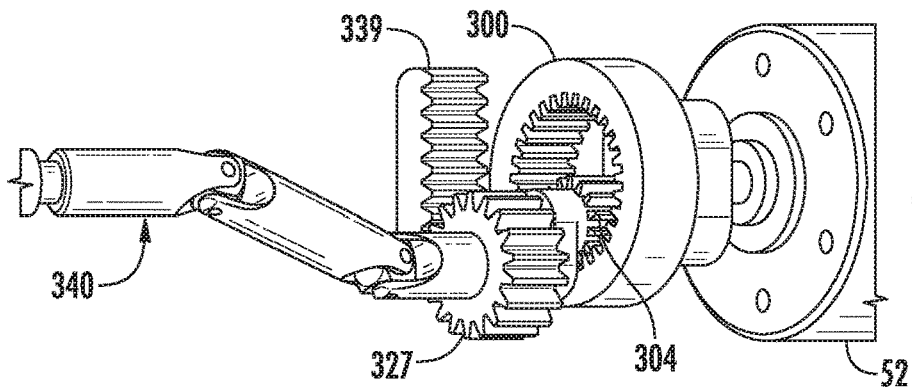
Figure 18D:
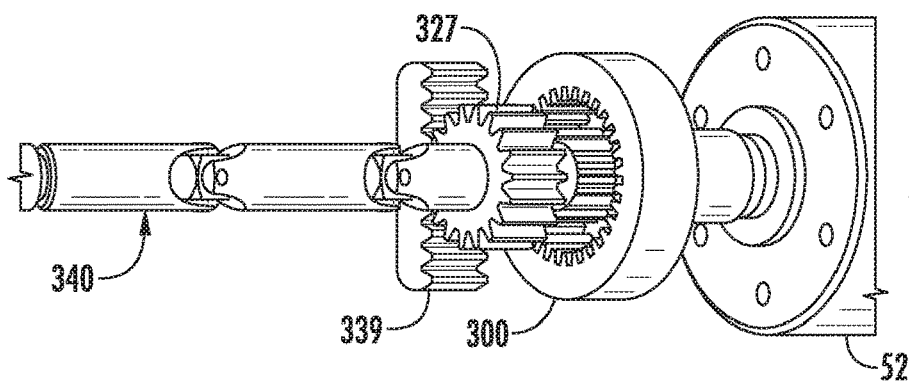

FIGS. 7A, 7B illustrate another form of drivers 37, 39. The first driver 37 is illustrated as a Cardan type drive that is operable to effect rotary oscillation of the shaft 36. While the structure shown in these Figures effects only oscillating rotation, the additional structure shown in FIGS. 17, 18 shows a mechanism to convert the oscillating rotation into oscillating rotation and linear reciprocation of the shaft 36.

FIG. 7A illustrates the basic functioning of a Cardan mechanism. An internal gear member 300 has an external gear 304 received therein. The gear ratio between the internal gear 300 and the external gear 304 is 2:1. The gear 300, in this case, is fixed against movement, while the gear 304 is part of a crank arm 306 mounted to motor 52. As the crank arm 306 effects revolving of the gear 304 about the center of rotation of the motor shaft, the gear 304 moves about the interior of the internal gear 300. The gear 304 has secured thereto an output arm 308 that has a center of rotation that is coaxial with the center of rotation of the motor 52 when the arm 308 is at its center position within the gear 300, as seen in FIG. 7A2-7A9. In this type of mechanism, the center of the arm 308 moves in a linear path in a laterally reciprocating manner. Thus, rotary output motion of the motor shaft can be converted into reciprocating linear motion. This can be seen in FIG. 17.

As seen in FIG. 7B, the Cardan style first driver 37 is coupled to a follower 320 that is operable to convert the linear movement of the arm 308 into oscillating rotary motion of the shaft 36. The illustrated follower 320 receives the arm 308 in an elongate slot (not shown) on the side facing the motor 52; this allows the arm 308 to move freely as the follower 320 pivots about a pair of pivot pins 322 that are mounted in suitable bearings (not shown) in the housing 32 and/or its nose 57. As the arm 308 moves laterally, as seen in FIG. 7A, it will force the follower 320 to pivot. A curved gear rack 325 is secured to the follower 320, is preferably integral therewith, and has the gear teeth spaced radially outwardly from the pivot pins 322. The radius of the gear rack 325 is substantially the radial distance of the gears from the center of rotation of the pivot pins 322. The gear rack 325 is meshed with a gear or gear segment 327, such as a spur gear that is secured to the shaft 36. As the follower 320 oscillates about its pivot pins 322, the shaft 36 is driven in a rotary oscillating manner.

FIGS. 17 and 18A-18D illustrate a still further embodiment of a second driver 39. It utilizes a Cardan first driver 37 such as shown in FIG. 7B. However, instead of a curved gear rack 325, this form uses a straight gear rack 339, and the gear 327 which is coupled to the shaft 36 moves laterally with its center of rotation being in a straight line. This can be accomplished by having the arm 308 centered on the center of rotation of the gear 304. The gear 327 is coupled to the shaft 36 through the use of a drive shaft 340. As shown, the drive shaft 340 has three sections 341, 343, and 345. Section 341 is secured to the shaft 36, which, in turn, is mounted in the bearing 59, as described above. Section 343 is coupled to section 341 in a manner that allows the axes of sections 341 and 343 to change their angular orientation. This can be accomplished by a universal joint (u-joint) 350. Section 343 is coupled to section 345 in a similar manner, as with a second universal joint 350. As the gear 327 rotates and moves laterally side-by-side on the gear rack 339, the length of the drive shaft 340 increases and decreases, effecting linear reciprocating movement of the shaft 36. This can be seen in FIGS. 18A-18D.

As used herein, the term "about" relating to angles A and B and rotation amounts takes into account manufacturing tolerances, anticipated wear during use, precision of fit between mating parts, and the rotation needed for a particular cutting tool 38 for a particular kind of material to be removed, and even adjacent material that might inadvertently engage the cutter to reduce the risk of damage.

All patents and publications mentioned in this specification are indicative of the levels of those skilled in the art to which the invention pertains. All patents and publications are herein incorporated by reference to the same extent as if each individual publication was specifically and individually indicated to be incorporated by reference.

It is to be understood that while a certain form of the invention is illustrated, it is not to be limited to the specific form or arrangement herein described and shown. It will be apparent to those skilled in the art that various changes may be made without departing from the scope of the invention, and the invention is not to be considered limited to what is shown and described in the specification and any drawings/figures included herein.

One skilled in the art will readily appreciate that the present invention is well adapted to carry out the objectives and obtain the ends and advantages mentioned, as well as those inherent therein. The embodiments, methods, procedures and techniques described herein are presently representative of the preferred embodiments, are intended to be exemplary, and are not intended as limitations on the scope. Changes therein and other uses will occur to those skilled in the art which are encompassed within the spirit of the invention and are defined by the scope of the appended claims. Although the invention has been described in connection with specific preferred embodiments, it should be understood that the invention as claimed should not be unduly limited to such specific embodiments. Indeed, various modifications of the described modes for carrying out the invention which are obvious to those skilled in the art are intended to be within the scope of the following claims.

What is claimed is:

1. A surgical tool having a cutter that rotary oscillates and linearly reciprocates, said surgical tool including:
    a handle;
    a motor associated with said handle, said motor providing continuous rotary motion;
    a transmission operably coupled to said motor, said motor being operable for selectively driving said transmission, said transmission having a first driver coupled to said motor and operable to effect rotary oscillation of a cutter shaft about a longitudinal axis of said cutter shaft, said transmission having a second driver coupled to said first driver operationally downstream thereof, said second driver including a helical bearing coupled to said cutter shaft and being operable in response to rotary oscillation of said cutter shaft effected by said first driver to effect linear reciprocation of said cutter shaft along said longitudinal axis and transmit said rotary oscillating rotation driving from said first driver to said cutter shaft, said helical bearing including an inner race secured to said cutter shaft and operable to move rotationally and oscillationally with said shaft;
    said cutter shaft having a cutter on a distal end thereof, said cutter shaft being mounted to a transmission output for simultaneous oscillating rotation and linear reciprocation of said cutter respectfully about and along said longitudinal axis.

2. The surgical tool of claim 1 wherein said helical bearing including an outer race associated with said inner race and a plurality of bearing balls retained between said inner and outer races.

3. The surgical tool of claim 2 wherein said outer race being fixed against movement relative to said handle.

4. The surgical tool of claim 1 wherein the handle being configured to be mounted to a surgical robot.

5. The surgical tool of claim 1 including a housing, said handle being part of said housing and being configured to be gripped in a person's hand for use in a surgical procedure.

6. The surgical tool of claim 1 wherein motor being an electric motor.

7. The oscillating rotary and reciprocating surgical tool of claim 1 wherein said cutting tool is moved outward with respect to said housing when said cutting tool is rotated in a first direction and wherein said cutting tool is moved inward with respect to said housing when said cutting tool is rotated in an opposite direction.

8. The oscillating rotary and reciprocating surgical tool of claim 1 wherein said inner race includes a helical groove, a plurality of balls arranged to roll within said helical groove.

9. The oscillating rotary and reciprocating surgical tool of claim 1 wherein said helical bearing includes an outer bearing race, said outer bearing race secured to said housing so that said outer bearing race remains fixed in position with respect to said housing during rotation of an inner race.

10. The oscillating rotary and reciprocating surgical tool of claim 1 wherein said motor is pneumatic.

11. An oscillating rotary and reciprocating surgical tool including:
    a housing forming a handle;
    a motor mounted in the housing, said motor providing continuous rotary motion;
    a cutter shaft carried by the housing;
    a transmission mounted in the housing, said transmission including a first driver coupled to the motor and operable to produce oscillating rotation of said cutter shaft about a longitudinal axis of said cutter shaft and including a second driver coupled to the first driver and operable to effect reciprocating movement of said cutter shaft along said longitudinal axis while the cutter shaft is rotationally oscillating;
    said first driver being operably associated with the motor and coupling said motor to said second driver, said first driver being operable to effect oscillating rotation of said cutter shaft through the second driver and said second driver being coupled to said cutter shaft and operable to add reciprocating movement of said cutter shaft while said cutter shaft is rotationally oscillating said second driver includes a helical bearing to cause said inward movement and said outward movement of said cutting tool in response to rotational oscillating movement of said cutting tool, said helical bearing includes a bearing race having a helical groove, a plurality of balls arranged to roll within said helical groove, said bearing race is an inner bearing race secured to said cutter shaft, said cutter shaft causing rotation of said inner bearing race; and
    a cutting tool mounted at a distal end of said cutter shaft and movable therewith in a rotationally oscillating manner and a reciprocating manner.

12. The oscillating rotary and reciprocating surgical tool of claim 11 wherein said cutting tool is moved outward with respect to said housing when said cutting tool is rotated in a first direction and wherein said cutting tool is moved inward with respect to said housing when said cutting tool is rotated in an opposite direction.

13. The oscillating rotary and reciprocating surgical tool of claim 11 wherein said helical bearing includes an outer bearing race, said outer bearing race secured to said housing so that said outer bearing race remains fixed in position with respect to said housing during rotation of said inner race.

14. The oscillating rotary and reciprocating surgical tool of claim 11 wherein said motor is electric.

15. The oscillating rotary and reciprocating surgical tool of claim 11 wherein said motor is pneumatic.

16. The oscillating rotary and reciprocating surgical tool of claim 11 wherein said first driver includes a drive arm secured to an output shaft of said motor, said drive arm offset radially from a center of rotation of said motor output shaft, a follower assembly restricted to planar reciprocating movement in response to rotation of said drive arm, said follower assembly drivingly coupled to said second driver to cause oscillating rotation to said cutter shaft.

17. The oscillating rotary and reciprocating surgical tool of claim 16 wherein follower assembly includes a plurality of gear teeth arranged in a linear arrangement defining a gear rack, said cutter shaft including a pinion gear constructed to intermesh with said follower assembly gear teeth.

\* \* \* \* \*